United States Patent [19]
Trimble et al.

[11] Patent Number: 6,150,506
[45] Date of Patent: *Nov. 21, 2000

[54] MODIFIED HEMOGLOBIN-LIKE COMPOUNDS AND METHODS OF PURIFYING SAME

[75] Inventors: Stephen P. Trimble; Antony J. Mathews, both of Boulder; Bruce A. Kerwin, Lafayette; David A. Marquardt, Longmont, all of Colo.; Spencer Anthony-Cahill, Bellingham, Wash.; Janet K. Epp, Boulder, Colo.; Dominic G. Madril, Loveland, Colo.; David C. Anderson, San Bruno, Calif.

[73] Assignee: Baxter Biotech Technology Sàrl, Neuchatel, Switzerland

[*] Notice: This patent is subject to a terminal disclaimer.

[21] Appl. No.: 08/973,629

[22] PCT Filed: Jun. 6, 1996

[86] PCT No.: PCT/US96/10420

§ 371 Date: Aug. 24, 1998

§ 102(e) Date: Aug. 24, 1998

[87] PCT Pub. No.: WO96/40920

PCT Pub. Date: Dec. 19, 1996

Related U.S. Application Data

[62] Continuation-in-part of application No. 08/487,431, Jun. 7, 1995, Pat. No. 5,844,090, which is a continuation-in-part of application No. 08/240,712, filed as application No. PCT/US92/09752, Nov. 6, 1992, Pat. No. 5,599,907, which is a continuation-in-part of application No. 07/789,179, Nov. 8, 1991, Pat. No. 5,545,727, which is a continuation-in-part of application No. PCT/US90/02654, May 10, 1990, which is a continuation-in-part of application No. 07/379,116, Jul. 13, 1989, abandoned, and a continuation-in-part of application No. 07/374,161, Jun. 30, 1989, abandoned, and a continuation-in-part of application No. 07/349,623, May 10, 1989, abandoned.

[51] Int. Cl.$^7$ .................. C07K 14/805; A61K 35/14

[52] U.S. Cl. .................. 530/385; 530/361; 435/69.1

[58] Field of Search .................. 435/69.7, 69.1, 435/69.6, 440, 252.3, 254.11, 71.1, 320.1, 325; 530/385, 829, 350, 380, 402, 408, 412, 416, 361; 536/23.5, 23.4; 514/832; 252/182.11, 183.11

[56] References Cited

U.S. PATENT DOCUMENTS

| | | | |
|---|---|---|---|
| 4,001,200 | 1/1977 | Bonsen et al. | 530/385 |
| 4,001,401 | 1/1977 | Bonsen et al. | 514/6 |
| 4,053,590 | 10/1977 | Bonsen et al. | 514/6 |
| 4,529,719 | 7/1985 | Tye | 514/6 |
| 4,584,130 | 4/1986 | Bucci et al. | 530/385 |
| 4,598,064 | 7/1986 | Walder | 514/6 |
| 4,600,531 | 7/1986 | Walder | 530/385 |
| 4,777,244 | 10/1988 | Bonhard et al. | 530/385 |
| 5,028,588 | 7/1991 | Hoffman et al. | 514/6 |
| 5,239,061 | 8/1993 | Fronticelli et al. | 530/385 |
| 5,844,090 | 12/1998 | Anderson et al. | 530/385 |

FOREIGN PATENT DOCUMENTS

| | | |
|---|---|---|
| 9013645 | 11/1990 | WIPO . |
| 9116349 | 10/1991 | WIPO . |
| 9211283 | 7/1992 | WIPO . |
| 9222646 | 12/1992 | WIPO . |
| 9308831 | 5/1993 | WIPO . |
| 9309143 | 5/1993 | WIPO . |

OTHER PUBLICATIONS

Winslow, R.M./Hemoglobin–Based Red Cell Substitutes/The Johns Hopkins U. Press/Baltimore/1992/Entire Text.

Snyder et al./HbXL99α: A Hemoglobin Derivative that is Cross–Linked Between the α Subunits is Useful as a Blood Substitute/PNAS USA/(1987) 84: 7280–7284.

Ishimoto et al/A Variant Hemoglobin Found in Macaca Fuscata: Another Polymerizing Hemoglogin of Macaques/J. Anthrop. Soc. Nippon/(1975) 83(3): 233–243.

Adams et al./HB Mississippi [β44(CD3)Ser→Arg]: A New Variant with Anomalous Properties/Hemoglobin/(1987) 11(5): 435–452.

Boneventura & Riggs/Polymerization of Hemoglobins of Mouse and Man: Structural Basis/Science/(1967) 149: 800–802.

Chatterjee et al./Isolation and Charaterization of a New Hemoglobin Derivative Crosslinked Between the α Chains (Lysine 99$α_1$→Lysine 99$α_2$)/J. Biol. Chem./(1986) 261: 9927–9937.

De Boer et al/The Tac Promoter: A Functional Hybrid Derived from the Trp and Lac Promoters/PNAS USA/(1983) 80: 21–25.

Greer & Perutz/Three Dimensional Structure of Haemoglobin Rainier/Nature New Biology/(1971) 230: 261–264.

Kavanaugh, et al./Affinity Labeling of Hemoglobin with 4,4'–Diisothiocyanostilbene,2,2'–Disulfonate: Covalent Cross–Linking in the 2,3–Diphosphoglycerate Binding Site/Biochemistry/(1988) 27: 1804–1808.

Looker et al/A Human Recombinant Haemoglobin Designed for Use as a Blood Substitute/Nature/(1992) 356: 258–260.

Manning et al./Evolution of a Polymeric Globin in the Brine Shrimp Artemia/Nature/(1990) 348: 653–656.

Riggs, A./Hemoglobin Polymerization in Mices/Science/(1965) 147: 621–623.

Simoni et al./Chromatographic Analysis of Biopolymers Distribution in "Poly–Hemoglobin", an Intermolecularly Crosslinked Hemoglogin Solution/Anal. Chim. Acta./(1993) 279: 73–88.

(List continued on next page.)

*Primary Examiner*—David Guzo
*Assistant Examiner*—Jon Shuman
*Attorney, Agent, or Firm*—Senniger, Powers, Leavitt & Roedel

[57] ABSTRACT

The present invention relates to modified hemoglobin-like polypeptides containing multiple dialpha (or dibeta) domains. The present invention also relates to multimeric hemoglobin-like proteins comprising covalently joined hemoglobin-like moieties. Another aspect of the inention is directed at a purification method of hemoglobin-like polypeptides utilizing ion exchange chromatography.

10 Claims, No Drawings

OTHER PUBLICATIONS

Takenaka et al./Hemoglobin IZU (Macaca): β83 (EF 7) Gly→Cys. A New Hemoglobin Variant Found in the Japanese Monkey (*Macaca fuscata*)/Biochem. Biophys. Acta/ (1977) 492: 433–444.

Tam et al./The Hemoglobins of the Bullfrog *Rana catesbeiana*/J. Biol. Chem./(1986) 261: 8290–8294.

Tondo et al./Functional Properties of Hemoglobin Porto Alegre ($\alpha_2^A \beta_2^{9Ser \to Cys}$) and the Reactivity of its Extra Cysteinyl Residue/Biochem. Biophys. Acta/(1974) 342:15–20.

Tondo, C.V./Osmometric Study of the Subunit Dissociation of Hemoglobin Porto Alegre [β9(A6)Ser→Cys] Disulfide Polymer/An. Acad. Bras. Cr./(1987) 59:243–251.

Honig et al./Hemoglobin Nigeria α–81 Ser→Cys): A New Variant Associated with α–Thalassemia(Blood/(1980) 55(1): 131–137.

```
                        SEQUENCE LISTING

<160> NUMBER OF SEQ ID NOS: 25

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence :Peptide
      linker to couple dialpha domains
<220> FEATURE:
<223> OTHER INFORMATION: Description of Artificial Sequence :Peptide
      linker to couple dialpha domains
<220> FEATURE:
<223> OTHER INFORMATION: Description of Artificial Sequence: Peptide
      linker to couple dialpha domains

<400> SEQUENCE: 1

Ser Gly Gly Ser Gly Gly Ser
  1               5

<210> SEQ ID NO 2
<211> LENGTH: 14
<212> TYPE: PRT
<213> ORGANISM: Artificial Sequence
<220> FEATURE:
<223> OTHER INFORMATION: Description of Artificial Sequence :Peptide
      linker to couple dialpha domains
<220> FEATURE:
<223> OTHER INFORMATION: Description of Artificial Sequence: Peptide
      linker to couple dialpha domains

<400> SEQUENCE: 2

Gly Gly Ser Gly Gly Ser Gly Gly Ser Gly Gly Ser Gly Gly
  1               5                  10

<210> SEQ ID NO 3
<211> LENGTH: 16
<212> TYPE: PRT
<213> ORGANISM: Artificial Sequence
<220> FEATURE:
<223> OTHER INFORMATION: Description of Artificial Sequence :Peptide
      linker to couple dialpha domains
<220> FEATURE:
<223> OTHER INFORMATION: Description of Artificial Sequence: Peptide
      linker to couple dialpha domains

<400> SEQUENCE: 3
```

```
Ser Gly Gly Ser Gly Gly Ser Gly Gly Ser Gly Gly Ser Gly Gly Ser
  1               5                  10                  15
```

<210> SEQ ID NO 4
<211> LENGTH: 45
<212> TYPE: DNA
<213> ORGANISM: Artificial Sequence
<220> FEATURE:
<223> OTHER INFORMATION: Description of Artificial Sequence:
      Oligonucleotide or 3' primer for generation of a
      alpha gene with Xba I site

<400> SEQUENCE: 4
cgggaatacg gtctagatca ttaacggtat ttcgaagtca gaacg         45

<210> SEQ ID NO 5
<211> LENGTH: 95
<212> TYPE: DNA
<213> ORGANISM: Artificial Sequence
<220> FEATURE:
<223> OTHER INFORMATION: Description of Artificial Sequence:
      Oligonucleotide or primer for generation of tac
      promotor with Bam HI-EagI site

<400> SEQUENCE: 5
gatccgagct gttgacaatt aatcatcggc tcgtataatg tgtggaattg tgacggataa    60
caatttcaca caggaaatta attaatgctg tctcc                              95

<210> SEQ ID NO 6
<211> LENGTH: 96
<212> TYPE: DNA
<213> ORGANISM: Artificial Sequence
<220> FEATURE:
<223> OTHER INFORMATION: Description of Artificial Sequence:
      Oligonucleotide or primer for generation of tac
      promotor with Bam HI-EagI site

<400> SEQUENCE: 6
ggccggagac agcattaatt aatttcctgt gtgaaattgt tatccgctca caattccaca    60
cattatacga gccgatgatt aattgtcaac agctcg                             96

<210> SEQ ID NO 7
<211> LENGTH: 64
<212> TYPE: DNA
<213> ORGANISM: Artificial Sequence
<220> FEATURE:
<223> OTHER INFORMATION: Description of Artificial Sequence:
      Oligonucleotide or 5' primer for generation of an
      alpha gene with EcoRI, BamHI and EagI sites

<400> SEQUENCE: 7
tcggattcga attccaagct gttggatcct tagattgaac tgtctccggc cgataaaacc    60
accg                                                                64

<210> SEQ ID NO 8
<211> LENGTH: 55
<212> TYPE: DNA
<213> ORGANISM: Artificial Sequence
<220> FEATURE:
<223> OTHER INFORMATION: Description of Artificial Sequence:
      Oligonucleotide or 5' primer for generation of a
      beta gene with Xba site

<400> SEQUENCE: 8
cggaagccca atctagagga aataatatat gcacctgact ccggaagaaa aatcc         55

```
<210> SEQ ID NO 9
<211> LENGTH: 44
<212> TYPE: DNA
<213> ORGANISM: Artificial Sequence
<220> FEATURE:
<223> OTHER INFORMATION: Description of Artificial Sequence:
      Oligonucleotide or 3' primer for generation of a
      beta gene with Hind III site

<400> SEQUENCE: 9
cccgaaacca agcttcatta gtgagctagc gcgttagcaa cacc              44

<210> SEQ ID NO 10
<211> LENGTH: 37
<212> TYPE: DNA
<213> ORGANISM: Artificial Sequence
<220> FEATURE:
<223> OTHER INFORMATION: Description of Artificial Sequence:
      Oligonucleotide or reverse primer for mutagenesis
      in a beta gene

<400> SEQUENCE: 10
tttaagctta attagtggta tttgtgagct agcgcgt                      37

<210> SEQ ID NO 11
<211> LENGTH: 37
<212> TYPE: DNA
<213> ORGANISM: Artificial Sequence
<220> FEATURE:
<223> OTHER INFORMATION: Description of Artificial Sequence:
      Oligonucleotide or reverse primer for mutagenesis
      in a alpha gene

<400> SEQUENCE: 11
cagcattaat taacctcctt agtgaaattg ttatccg                      37

<210> SEQ ID NO 12
<211> LENGTH: 45
<212> TYPE: DNA
<213> ORGANISM: Artificial Sequence
<220> FEATURE:
<223> OTHER INFORMATION: Description of Artificial Sequence:
      Oligonucleotide or reverse primer for mutagenesis
      in a beta gene

<400> SEQUENCE: 12
ggtgcatata tttacctcct tatctagatc attaacggta tttcg             45

<210> SEQ ID NO 13
<211> LENGTH: 10
<212> TYPE: DNA
<213> ORGANISM: Artificial Sequence
<220> FEATURE:
<223> OTHER INFORMATION: Description of Artificial Sequence:
      Oligonucleotide or primer for generation of a Pme
      I linker in pSelect-1

<400> SEQUENCE: 13
ggtttaaacc                                                    10

<210> SEQ ID NO 14
<211> LENGTH: 58
<212> TYPE: DNA
<213> ORGANISM: Artificial Sequence
<220> FEATURE:
<223> OTHER INFORMATION: Description of Artificial Sequence:
      Oligonucleotide or 5' primer for production of a
      lacI gene with Hind III and Not I sites
```

-continued

```
<400> SEQUENCE: 14
ggcgaataaa agcttgcggc cgcgttgaca ccatcgaatg gcgcaaaacc tttcgcgg        58

<210> SEQ ID NO 15
<211> LENGTH: 69
<212> TYPE: DNA
<213> ORGANISM: Artificial Sequence
<220> FEATURE:
<223> OTHER INFORMATION: Description of Artificial Sequence:
      Oligonucleotide or 3' primer for production of a
      IacI gene with bam HI site

<400> SEQUENCE: 15
gggcaaatag gatccaaaaa aaagcccgct cattaggcgg gctttatcac tgcccgcttt        60
ccagtcggg                                                               69

<210> SEQ ID NO 16
<211> LENGTH: 54
<212> TYPE: DNA
<213> ORGANISM: Artificial Sequence
<220> FEATURE:
<223> OTHER INFORMATION: Description of Artificial Sequence:
      Oligonucleotide or 5' primer for production of a
      pBR332 ori with Bam HI and Not I sites

<400> SEQUENCE: 16
ccccgaaaag gatccaagta gccggcggcc gcgttccact gagcgtcaga cccc             54

<210> SEQ ID NO 17
<211> LENGTH: 42
<212> TYPE: DNA
<213> ORGANISM: Artificial Sequence
<220> FEATURE:
<223> OTHER INFORMATION: Description of Artificial Sequence:
      Oligonucleotide or 3' primer for generation of
      pBR332 ori with PmeI site

<400> SEQUENCE: 17
ggcggtcctg tttaaacgct gcgctcggtc gttcggctgc gg                          42

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide or primer for introduction of SpeI
      site in the end of dialpha domains

<400> SEQUENCE: 18
accgttctga ctagtaaata ccgttaatga                                        30

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide or primer for introduction of Pst
      I site in dialpha genes and for removal of SpeI
      site in a beta domain

<400> SEQUENCE: 19
ggaggttaat taatgctgtc tcctgcagat                                        30
```

```
<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide or primer for introduction of Pst
      I site in dialpha genes and for removal of SpeI
      site in a beta domain

<400> SEQUENCE: 20
ctggtgggta aagttctggt ttgcgttctg                                   30

<210> SEQ ID NO 21
<211> LENGTH: 50
<212> TYPE: DNA
<213> ORGANISM: Artificial Sequence
<220> FEATURE:
<223> OTHER INFORMATION: Description of Artificial Sequence:
      Oligonucleotide or primer for introduction of 7
      amino acid fusion peptide linker connecting two
      dialpha globins

<400> SEQUENCE: 21
ctagtaaata ccgatcgggt ggctctggcg gttctgttct gtctcctgca             50

<210> SEQ ID NO 22
<211> LENGTH: 42
<212> TYPE: DNA
<213> ORGANISM: Artificial Sequence
<220> FEATURE:
<223> OTHER INFORMATION: Description of Artificial Sequence:
      Oligonucleotide or primer for introduction of 7
      amino acid fusion peptide linker connecting two
      dialpha globins

<400> SEQUENCE: 22
ggagacagaa cagaaccgcc agagccaccc gatcggtatt ta                     42

<210> SEQ ID NO 23
<211> LENGTH: 67
<212> TYPE: DNA
<213> ORGANISM: Artificial Sequence
<220> FEATURE:
<223> OTHER INFORMATION: Description of Artificial Sequence:
      Oligonucleotide for introduction of convenient
      restriction sites in place of a deleted lacI gene

<400> SEQUENCE: 23
ggccgcctta agtacccggg tttctgcaga aagcccgcct aatgagcggg cttttttttc  60
cttaggg                                                            67

<210> SEQ ID NO 24
<211> LENGTH: 67
<212> TYPE: DNA
<213> ORGANISM: Artificial Sequence
<220> FEATURE:
<223> OTHER INFORMATION: Description of Artificial Sequence:
      Oligonucleotide for introduction of convenient
      restriction sites in place of a deleted lacI gene

<400> SEQUENCE: 24
gatcccctaa ggaaaaaaaa gcccgctcat taggcgggct ttctgcagaa acccgggtac  60
ttaaggc                                                            67

<210> SEQ ID NO 25
<211> LENGTH: 4
```

```
<212> TYPE: PRT
<213> ORGANISM: Artificial Sequence
<220> FEATURE:
<223> OTHER INFORMATION: Ile is acetate - Ile
<220> FEATURE:
<223> OTHER INFORMATION: Description of Artificial Sequence: peptide
      reagent

<400> SEQUENCE: 25

Ile Glu Gly Arg
```

MODIFIED HEMOGLOBIN-LIKE COMPOUNDS AND METHODS OF PURIFYING SAME

This application is the U.S. national phase of International Application No. PCT/US96/10420, filed Jun. 6, 1996, which is a continuation-in-part of U.S. patent application Ser. No. 08/487,431, filed Jun. 7, 1995, now U.S. Pat. No. 5,844,090, which is a continuation-in-part of U.S. patent application Ser. No. 08/240,712, filed May 9, 1994, now U.S. Pat No. 5,599,907, which was the U.S. national phase of International application No. PCT/US92/09752, filed Nov. 6, 1992., which is a continuation in part of U.S. patent application Ser. No. 07/789,179, filed Nov. 8, 1991, now U.S. Pat. No. 5,545,727, which is a continuation in part of PCT/US90/02654, filed May 10, 1990, which is a continuation in part of U.S. patent application Ser. No. 07/379,116, filed Jul. 13, 1989, now abandoned, U.S. application Ser. No. 07/374,161, filed Jun. 30, 1989, now abandoned, and U.S. patent application Ser. No. 07/349,623, filed May 10, 1989, now abandoned.

BACKGROUND OF THE INVENTION

The present invention is directed to modified hemoglobin-like compounds, and more particularly to modified hemoglobin-like polypeptides and proteins. The present invention is directed also to methods of purifying such modified hemoglobin-like compounds.

Hemoglobin (referred to herein as "Hb") is the oxygen-carrying component of blood. Hemoglobin circulates through the bloodstream inside small enucleate cells called erythrocytes (red blood cells). Hemoglobin is a protein constructed from four associated polypeptide chains, and bearing prosthetic groups known as hemes. The erythrocyte helps maintain hemoglobin in its reduced, functional form. The heme iron atom is susceptible to oxidation, but may be reduced again by one of two enzyme systems within the erythrocyte, the cytochrome $b_5$ and glutathione reduction systems.

Hemoglobin binds oxygen at a respiratory surface (skin, gills, trachea, lung, etc.) and transports the oxygen to inner tissues, where it is released and used for metabolism. In nature, low molecular weight hemoglobins (16–120 kilodaltons) tend to be enclosed in circulating red blood cells, while the larger polymeric hemoglobins circulate freely in the blood or hemolymph.

The structure of hemoglobin is well known as described in Bunn & Forget, eds., *Hemoglobin: Molecular, Genetic and Clinical Aspects* (W. B. Saunders Co., Philadelphia, Pa.: 1986) and Fermi & Perutz "Hemoglobin and Myoglobin," in Phillips and Richards, *Atlas of Molecular Structures in Biology* (Clarendon Press: 1981).

About 92% of normal adult human hemolysate is Hb $A_o$ (designated alpha$_2$ beta$_2$ because it comprises two alpha and two beta chains). In a hemoglobin tetramer, each alpha subunit is associated with a beta subunit to form a stable alpha/beta dimer, two of which in turn associate to form the tetramer. The subunits are noncovalently associated through Van der Waals forces, hydrogen bonds and salt bridges. The amino add sequences of the alpha and beta globin polypeptide chains of Hb $A_o$ are given in Table 1 of PCT Publication No. WO 93/09143. The wild-type alpha chain consists of 141 amino acids. The iron atom of the heme (ferroprotoporphyrin IX) group is bound covalently to the imidazole of His 87 (the "proximal histidine"). The wild-type beta chain is 146 residues long and heme is bound to it at His 92.

The human alpha and beta globin genes reside on chromosomes 16 and 11, respectively. Bunn and Forget, infra at 172. Both genes have been cloned and sequenced, Liebhaber, et al., *PNAS* 77: 7054–58 (1980) (alpha-globin genomic DNA); Marotta, et al., *J. Biol. Chem.*, 252:5040–53 (1977) (beta globin cDNA); Lawn, et al., *Cell,* 21:647 (1980) (beta globin genomic DNA).

Hemoglobin exhibits cooperative binding of oxygen by the four subunits of the hemoglobin molecule (the two alpha globins and two beta globins in the case of Hb $A_o$), and this cooperativity greatly facilitates efficient oxygen transport. Cooperativity, achieved by the so-called heme-heme interaction, allows hemoglobin to vary its affinity for oxygen. Cooperativity can also be determined using the oxygen dissociation curve (described below) and is generally reported as the Hill coefficient, "n" or "$n_{max}$." Hemoglobin reversibly binds up to four moles of oxygen per mole of hemoglobin.

Oxygen-carrying compounds are frequently compared by means of a device known as an oxygen dissociation curve. This curve is obtained when, for a given oxygen carrier, oxygen saturation or content is graphed against the partial pressure of oxygen. For Hb, the percentage of saturation increases with partial pressure according to a sigmoidal relationship. The $P_{50}$ is the partial pressure at which the oxygen-carrying species is half saturated with oxygen. It is thus a measure of oxygen-binding affinity; the higher the $P_{50}$, the more readily oxygen is released.

The ability of hemoglobin to alter its oxygen affinity under physiological conditions, increasing the efficiency of oxygen transport around the body, is largely dependent on the presence of the metabolite 2,3-diphosphoglycerate (2,3-DPG). The oxygen affinity of hemoglobin is lowered by the presence of 2,3-DPG. Inside the erythrocyte 2,3-DPG is present at a concentration nearly as great as that of hemoglobin itself. In the absence of 2,3-DPG "conventional" hemoglobin (hemoglobin $A_o$) binds oxygen very strongly at physiological oxygen partial pressures and would release little oxygen to respiring tissue. Accordingly, any substitute for hemoglobin must somehow correct the oxygen affinity and/or the Hill coefficient to physiologically meaningful levels (see e.g., Rausch, C. and Feola, M., U.S. Pat. Nos. 5,084,558 and 5,296,465; Sehgal, L. R., U.S. Pat. Nos. 4,826,811 and 5,194,590; Hoffman et al., WO 90/13645; Hoffman and Nagai, U.S. Pat. No. 5,028,588; Anderson et al., WO 93/09143; Fronticelli, C. et al., U.S. Pat. No. 5,239,061; and De Angelo et al., WO 93/08831 and WO 91/16349).

It is not always practical or safe to transfuse a patient with donated blood. In these situations, use of a red blood cell ("RBC") substitute is desirable. When human blood is not available or the risk of transfusion is too great, plasma expanders can be administered. However, plasma expanders, such as colloid and crystalloid solutions, replace only blood volume, and not oxygen carrying capacity. In situations where blood is not available for transfusion, a red blood cell substitute that can transport oxygen in addition to providing volume replacement is desirable.

To address this need, a number of red blood cell substitutes have been developed (Winslow, R. M.(1992) *Hemoglobin-based Red Cell Substitutes,* The Johns Hopkins University Press, Baltimore 242 pp). These substitutes include synthetic perfluorocarbon solutions, (Long, D. M. European Patent 0307087), stroma-free hemoglobin solutions, both chemically crosslinked and uncrosslinked, derived from a variety of mammalian red blood cells (Rausch, C. and Feola, M., U.S. Pat. Nos. 5,084,558 and 5,296,465; Sehgal, L. R., U.S. Pat. Nos. 4,826,811 and 5,194,590; Vlahakes, G. J. et al., (1990) *J. Thorac. Cardiovas. Surg.* 100: 379–388) and hemoglobins expressed in and purified from genetically engineered organisms (for example, non-erythrocyte cells such as bacteria and yeast, Hoffman et al., WO 90/13645; bacteria, Anderson et al., WO 93/09143, bacteria and yeast Fronticelli, C. et al., U.S. Pat. No. 5,239,061; yeast, De Angelo et al., WO 93/08831 and WO 91/16349; and transgenic mammals, Logan et al., WO 92/22646; Townes, T. M and McCune, S. L., WO 92/11283). These red blood cell substitutes have been designed to replace or augment the volume and the oxygen carrying capability of red blood cells.

However, red blood cell replacement solutions that have been administered to animals and humans have exhibited certain adverse events upon administration. These adverse reactions have included hypertension, renal failure, neurotoxicity, and liver toxicity (Winslow, R. M., (1992) *Hemoglobin-based Red Cell Substitutes,* The Johns Hopkins University Press, Baltimore 242 pp.; Biro, G. P. et al., (1992) *Biomat., Art. Cells & Immob. Biotech.* 20: 1013–1020). In the case of perfluorocarbons, hypertension, activation of the reticulo-endothelial system, and complement activation have been observed (Reichelt, H. et al., (1992) in *Blood Substitutes and Oxygen Carriers,* T. M. Chang (ed.), pg. 769–772; Bentley, P. K. supra, pp. 778–781). For hemoglobin-based oxygen carriers, renal failure and renal toxicity are the result of the formation of hemoglobin $\alpha/\beta$ dimers. The formation of dimers can be prevented by chemically crosslinking (Sehgal, et al., U.S. Pat. Nos. 4,826,811 and 5,194,590; Walder, J. A. U.S. Reissue Pat. RE34271) or genetically linking (Hoffman, et al, WO 90/13645) the hemoglobin dimers so that the tetramer is prevented from dissociating.

Prevention of dimer formation has not alleviated all of the adverse events associated with hemoglobin administration. Blood pressure changes and gastrointestinal effects upon administration of hemoglobin solutions have been attributed to vasoconstriction resulting from the binding of endothelium derived relaxing factor (EDRF) by hemoglobin (Spahn, D. R. et al., (1994) *Anesth. Analg.* 78: 1000–1021; Biro, G. P., (1992) *Biomat., Art. Cells & Immob. Biotech.,* 20: 1013–1020; Vandegriff, K. D. (1992) *Biotechnology and Genetic Engineering Reviews,* Volume 10: 404–453 M. P. Tombs, Editor, Intercept Ltd., Andover, England). Endothelium derived relaxing factor has been identified as nitric oxide (NO) (Moncada, S. et al., (1991) *Pharmacol. Rev.* 43: 109–142 for review); both inducible and constitutive NO are primarily produced in the endothelium of the vasculature and act as local modulators of vascular tone.

When hemoglobin is contained in red blood cells, it cannot move beyond the boundaries of blood vessels. Therefore, nitric oxide must diffuse to the hemoglobin in an RBC before it is bound. When hemoglobin is not contained within an RBC, such as is the case with hemoglobin-based blood substitutes, it may pass beyond the endothelium lining the blood vessels and penetrate to the extravascular space (extravasation). Thus, a possible mechanism causing adverse events associated with administration of extracellular hemoglobin may be excessive inactivation of nitric oxide due to hemoglobin extravasation. Furthermore, NO is constitutively synthesized by the vascular endothelium. Inactivation of NO in the endothelium and extravascular space may lead to vasoconstriction and the pressor response observed after infusions of cell-free hemoglobin. Larger hemoglobins may serve to reduce hypertension associated with the use of some extracellular hemoglobin solutions.

In addition to the effects noted above, the dosage of non-polymeric extracellular hemoglobin that can be administered may be limited by the colloidal osmotic pressure (COP) of the solution. Administration of an extracellular hemoglobin composed of hemoglobin tetramers that would have the same grams of hemoglobin as a unit of packed red blood cells might result in a significant influx of water from the cells into the blood stream due to the high colloid osmotic pressure of the hemoglobin solution. Polymeric hemoglobin solutions can be administered at higher effective hemoglobin dosages, because as the molecular weight increases, the number of the individual molecules is decreased, resulting in reduced COP (Winslow, R. M., (1992) *Hemoglobin-based Red Cell Substitutes,* The Johns Hopkins University Press, Baltimore, pp 34–35).

Some higher molecular weight hemoglobins occur in nature. For example, there are three mutants of human hemoglobin that are known to polymerize as a result of formation of intermolecular (first tetramer to second tetramer) disulfide bridges. Tondo, *Biochem. Biophys. Acta,* 342:15–20 (1974) and Tondo, *An. Acad. Bras. Cr.,* 59:243–251 (1987) describe one such mutant known as Hb Porto Alegre. Hb Mississippi is characterized by a cysteine substitution in place of Ser CD3(44)$\beta$ and is believed to be composed of ten or more hemoglobin tetramers according to Adams et al., *Hemoglobin,* 11(5):435–542 (1987). Hemoglobin Ta Li is characterized by a $\beta$83(EF7)Gly$\rightarrow$Cys mutation, which showed slow mobility in starch gel electrophoresis, indicating that it too was a polymer.

There are a few known naturally occurring mutants of non-polymerizing human hemoglobins that have a cysteine mutation that do not polymerize (Harris et al., *Blood,* 55(1):131–137 (1980)(Hemoglobin Nigeria); Greer et al., *Nature [New Biology],* 230:261–264 (1971) (Hemoglobin Rainier). Hemoglobin Nunobiki ($\alpha$ 141 Arg$\rightarrow$Cys) also features a non-polymerizing cysteine substitution. In both Hb Rainier and Hb Nunobiki, the mutant cysteine residues are surface cysteines.

Polymeric hemoglobins have also been reported in various vertebrates and invertebrates. Murine polymeric hemoglobins are described in Bonaventura & Riggs (*Science,* (1967)149:800–802) and Riggs (*Science,* (1965) 147:621–623). A polymerizing hemoglobin variant in macaque monkeys is reported in Takenaka et al., *Biochem Biophys. Acta,* 492:433–444 (1977); Ishimoto et al., *J. Anthrop. Soc. Nippon,* 83(3):233–243 (1975). Both amphibians and reptiles also possess polymerizing hemoglobins (Tam et al., *J. Biol. Chem.,* (1986) 261:8290–94).

Some invertebrate hemoglobins are also large multi-subunit proteins. The extracellular hemoglobin of the earthworm (*Lumbricus terrestris*) has twelve subunits, each of which is a dimer of structure $(abcd)_2$ where "a", "b", "c", and "d" denote the major heme containing chains. The "a", "b", and "c" chains form a disulfide-linked trimer. The whole molecule is composed of 192 heme-containing chains and 12 non-heme chains, and has a molecular weight of 3800 kDa. The brine shrimp Artemia produces three polymeric hemoglobins with nine genetically fused globin subunits (Manning, et al., *Nature,* (1990) 348:653). These are formed by variable association of two different subunit types, a and b. Of the eight intersubunit linkers, six are 12 residues long, one is 11 residues and one is 14 residues.

Non-polymerizing crosslinked hemoglobins have been artificially produced. For example, hemoglobin has been altered by chemically crosslinking the alpha chains between the Lys99 of alpha$_1$ and the Lys99 of alpha$_2$ (Walder, U.S.

Pat. Nos. 4,600,531 and 4,598,064; Snyder, et al., *PNAS (USA)* (1987) 84: 7280–84; Chatterjee, et al., *J. Biol. Chem.,* (1986) 261: 9927–37). The beta chains have also been chemically crosslinked (Kavanaugh, et al., *Biochemistry,* (1988) 27: 1804–8). U.S. Pat. No. 5,028,588 suggests that the T state of hemoglobin (corresponding to deoxygenated hemoglobin) may be stabilized by intersubunit (but intratetrameric) disulfide crosslinks resulting from substitution of cysteine residues for other residues.

Hemoglobin has also been artificially crosslinked to form polymers. For example, U.S. Pat. No. 4,001,401, U.S. Pat. No. 4,001,200, U.S. Pat. No. 4,777,244 and U.S. Pat. No. 4,053,590 all relate to polymerization of red blood cell-derived hemoglobin by chemical crosslinking. The crosslinking is achieved with the aid of bifunctional or polyfunctional crosslinking agents, especially those reactive with exposed amino groups of the globin chains. Aldehydes such as glutaraldehyde and glycolaldehyde have been used to crosslink hemoglobin both intramolecularly (within a tetramer) and intermolecularly (between tetramers). Intramolecular crosslinks serve to prevent dimerization into alpha/beta dimers and may also alter oxygen affinity, while intermolecular crosslinks create polymers of tetrameric hemoglobin. Polymeric hemoglobins may result in reduced extravasation because of their increased size. Reduced extravasation may, in turn, lead to reduced pressor effects resulting from infused hemoglobin solutions.

The result of these polymerization chemistries that have been used to crosslink hemoglobins is a polydisperse composition of covalently crosslinked aggregates. Bucci, U.S. Pat. No. 4,584,130, at col. 2, comments that "the polyhemoglobin reaction products are a heterogeneous mixture of various molecular species which differ in size and shape. The molecular weights of these polyhemoglobins range from 64,500 to 600,000 Daltons. The separation of individual molecular species from the heterogeneous mixture is virtually impossible. In addition, although longer retention times in vivo are obtained using polyhemoglobins, the oxygen affinity thereof is higher than that of stroma-free hemoglobin."

It is well recognized that random polymerization is difficult to control and that a number of different polymers can be obtained, commonly between two and ten tetramers per polymer. For example, according to Tye, U.S. Pat. No. 4,529,179, polymerized pyridoxylated hemoglobin has "a profound chemical heterogeneity making it difficult to study as a pharmaceutical agent."

Furthermore, once hemoglobin is polymerized, purification of specific molecular weight fractions can be accomplished using only molecular weight separation techniques. For example, tangential flow separation techniques can be used to separate certain size ranges of polymerized hemoglobins. However the membranes that are available for such separations are available only in a limited number of size ranges which allow the production of hemoglobins less than 100 kDa or greater than 300 kDa. In addition, such membranes are cumbersome, expensive, difficult to clean and the separation can be very slow.

Size exclusion chromatography (also known as, for example, gel filtration chromatography or gel permeation chromatography) has also been used in the past to separate hemoglobin molecular weight fractions. However, this technique is not suitable for large scale operation, and furthermore, does not provide good resolution for separation of molecular weight fractions (Simoni et al., (1993) *Anal. Chim. Acta,* 279: 73–88).

Simoni (1993, infra) also report the use of ion exchange chromatography to separate different molecular weight fractions of hemoglobin polymers. However, these workers noted that this kind of separation required differences in net charges. In addition, they used a salt gradient elution to separate the different molecular weight fractions, and they did not demonstrate any significant resolution of tetramer, octamer and decamer.

Correlations of molecular weight with serum half life for various proteins, such as IL-2, demonstrate that a significantly longer half life may be expected as the molecular weight of a protein increases, particularly above the renal filtration limit of 50–70 kDa. The use of crosslinkers that can inhibit the degradation of hemoglobin tetramers into dimers that are readily cleared can also lead to increased serum half life.

Accordingly, a need exists for additional hemoglobin-like compounds having these desired characteristics. In addition, a need exists for simple methods of creating specific molecular weight distributions in high molecular weight hemoglobin mixtures. The present invention satisfies these needs and provides related advantages.

SUMMARY OF THE INVENTION

The present invention relates to modified hemoglobin-like compounds. In one aspect, the invention is directed to globin-like polypeptides having multiple dialpha domains. Such polypeptides can contain two dialpha domains, also referred to herein as "di-dialpha" domains, or more. These globin-like polypeptides can be linked by a peptide linker having at least five amino acids between the dialpha domains, preferably at least seven amino adds. Preferably, the linkers are encoded by a peptide linker having Ser-Gly-Gly as a repeat unit, such as the amino acid sequences: Ser-Gly-Gly-Ser-Gly-Gly-Ser (SEQ.ID.NO.1); Gly-Gly-Ser-Gly-Gly-Ser-Gly-Gly-Ser-Gly-Gly-Ser-Gly-Gly (SEQ.ID.NO.2) and Ser-Gly-Gly-Ser-Gly-Gly-Ser-Gly-Gly-Ser-Gly-Gly-Ser-Gly-Gly-Ser (SEQ.ID.NO.3). The globin-like polypeptides can be recombinantly expressed in a host cell, such as *E. coli.* Di-dibeta globin-like polypeptides are analogously defined, and are a further aspect of the instant invention.

The invention also relates to nucleic add molecules having a nucleic add sequence encoding such globin-like polypeptides. In one embodiment, the nucleic acid molecules encode a globin-like polypeptide having two dialpha domains and a separate polypeptide having a single beta domain or a di-beta domain.

In another aspect, the present invention relates to a multimeric hemoglobin compound that comprises two dialpha globins that are connected through a peptide linker, wherein only one of the four alpha globin domains contains a non-naturally occurring cysteine residue (mono-cys di-dialpha). In a further aspect of this invention, such mono-cys di-dialpha-containing hemoglobin composition can be crosslinked directly or indirectly to another identical mono-cys di-dialpha or any other suitable hemoglobin-like molecule. Mono-cys di-dibeta molecules are analogously defined and also can be crosslinked as described herein.

In another aspect, the present invention also provides multimeric hemoglobin-like proteins in which a first hemoglobin-like moiety is directly attached to two or more other hemoglobin-like moieties. Compositions containing such multimeric hemoglobin-like proteins are also provided.

In a further aspect, the present invention relates to methods for making the multimeric hemoglobin-like proteins.

The methods are accomplished by:
(a) obtaining a first hemoglobin-like moiety having amino acids capable of attaching to one end of a heterobifunctional linker to form a core hemoglobin-like moiety;
(b) obtaining at least two other hemoglobin-like moieties having an amino acid capable of attaching to the other end of the heterobifunctional linker;
(c) contacting the heterobifunctional linker to the first hemoglobin-like moiety; and
(d) adding the other hemoglobin-like moieties to form the multimeric hemoglobin-like protein.

In a still further aspect, the present invention relates to methods for separation of molecular weight fractions of polymerized hemoglobin or hemoglobin-like molecules to obtain substantially monodisperse hemoglobin solutions. Such methods are accomplished by:
(a) contacting a polydisperse mixture of polymerized hemoglobin-like molecules with an ion exchange matrix;
(b) washing the ion exchange matrix with a first buffer;
(c) eluting the ion exchange matrix with a second buffer which may be the same or different than said first buffer to obtain a substantially monodisperse hemoglobin-like solution.

DETAILED DESCRIPTION OF THE INVENTION

The present invention generally relates to hemoglobin-like compounds comprised of novel globin-like polypeptides or hemoglobin-like proteins. These compounds contain various modifications to the naturally-occurring hemoglobins, particularly human Hb $A_o$. In a further aspect, the present invention relates to methods of purifying such hemoglobin-like molecules and other polymeric hemoglobin-like molecules.

As described above, most naturally-occurring human hemoglobins are constructed of four non-covalently linked polypeptide chains: two chains containing identical alpha domains and two chains containing identical beta domains. The novel globin-like polypeptides of the present invention, however, contain at least two dialpha (or two dibeta) domains in a single polypeptide chain. A "dialpha domain" (or "dibeta domain") consists of two alpha (or beta) domains (or polypeptide sequences) connected between the C-terminus of a first alpha domain (or beta domain) and the N-terminus of a second alpha domain (or beta domain) as described in PCT Publication No. WO 93/09143, incorporated herein by reference. Thus, the novel globin-like polypeptides have as a minimum four alpha (or beta) domains per polypeptide.

As used herein, the term "globin-like polypeptide" means a polypeptide having a domain that is substantially homologous with a globin subunit of a naturally occurring hemoglobin. For example, a globin-like polypeptide containing two dialpha domains means that each of the four alpha domains is substantially homologous to a native alpha globin or a mutant thereof differing from the native sequence by one or more substitutions, deletions or insertions, while remaining substantially homologous with the native alpha globin and retaining its ability to associate with a beta globin. As used herein, the term "alpha domain" is intended to include but not be limited to naturally occurring alpha globins, including normal human alpha globin, and mutants thereof. A "beta domain" is analogously defined. Subunits of vertebrate and invertebrate hemoglobins or mutants thereof which are sufficiently homologous with human alpha or beta globin are embraced by the terms "alpha or beta domains." For example, the subunits of bovine hemoglobin are within the scope of these terms.

In determining whether an alpha or beta globin contemplated by the present invention is substantially homologous to a particular wild-type alpha or beta globin, sequence similarity is an important but not exclusive criterion. Sequence similarity may be determined by conventional algorithms, which typically allow introduction of a small number of gaps in order to achieve the best fit. An alpha domain contemplated for use in the present invention will typically have at least about 75% sequence identity with wild-type human alpha globin, and greater homology with human alpha globin than with human beta globin. However, a polypeptide having an alpha domain of lesser sequence identity may still be considered "substantially homologous" with a wild-type alpha globin if it has a greater sequence identity than would be expected from chance and also has the characteristic higher structure (e.g., the "myoglobin fold") of alpha globin.

Mutations can be introduced to alter the oxygen affinity (or cooperativity, or activity with respect to pH, salt, temperature, or other environmental parameters) or stability (to heat, acid, alkali, or other denaturing agents) of the hemoglobin, to facilitate genetic fusion or crosslinking, or to increase the ease of expression and assembly of the individual chains. Guidance as to certain types of mutations is provided, for example, in U.S. Pat. No. 5,028,588 and PCT Publication No. WO 93/09143, both incorporated herein by reference. The present invention further includes molecules which depart from those taught herein by gratuitous mutations that do not substantially affect biological activity.

The dialpha (or dibeta) domains of the novel globin-like polypeptides can be connected by various means known in the art. For example, the domains can be coupled by a peptide linker between any two dialpha domains. A discussion of suitable distances is also provided in WO 93/09143, incorporated herein by reference. With knowledge of these distances, one skilled in the art can readily determine, for example through molecular modeling, the useful lengths of suitable peptide linkers. Particularly useful peptide linkers have at least five amino acids, preferably at least seven amino acids. The peptide linker can have an amino acid sequence that contains Ser-Gly-Gly as a repeating unit, as in the following illustrative amino add sequence: Ser-Gly-Gly-Ser-Gly-Gly-Ser (SEQ.ID.NO. 1). Examples of other amino acid sequences useful as peptide linkers containing this repeating unit include: Gly-Gly-Ser-Gly-Gly-Ser-Gly-Gly-Ser-Gly-Gly-Ser-Gly-Gly (SEQ.ID.No. 2) and Ser-Gly-Gly-Ser-Gly-Gly-Ser-Gly-Gly-Ser-Gly-Gly-Ser-Gly-Gly-Ser (SEQ.ID.No. 3).

The multiple dialpha domains and the peptide linkers of the globin-like polypeptides can be genetically fused through recombinant methods known in the art or as described, for example, in WO 93/09143 or in the Examples below. The preparation of a single dialpha globin as an intermediate product is also described in this publication.

The globin-like polypeptides can be used to prepare hemoglobin-like pseudomers. Such pseudomeric Hb-like proteins are described in WO 93/09143. Pseudomeric hemoglobin-like proteins have at least one more domain than the number of polypeptide chains, i.e., at least one polypeptide chain contains two or more globin-like domains.

It is also possible to introduce non-naturally occurring cysteine residues into one alpha subunit of a dialpha domain or one alpha subunit of a di-dialpha domain or larger dialpha domains to prepare other pseudomeric hemoglobin-like proteins. Preferably these non-naturally occurring cysteine residues are asymmetric, that is they occur in only one alpha domain of the longer di-dialpha polypeptide. Such mutations can also be incorporated in an analogous fashion in di-dibeta globins. The asymmetric cysteine residues can then be used to form direct disulfide bridges connecting the dialpha (or dibeta) domains or crosslinked by coupling reagents specific for cysteine residues to produce the larger pseudomeric Hb proteins.

The hemoglobin-like pseudomers can be purified by any suitable purification method known to those skilled in the art. Useful purification methods for the hemoglobin-like proteins of the present invention are taught in PCT Publication WO 95/14038, incorporated herein by reference. Briefly, the methods described therein involve an immobilized metal affinity chromatography resin charged with a divalent metal ion such as zinc, followed by anion exchange chromatography. According to this publication, the solution containing the desired Hb-containing material to be purified can first be heat treated to remove protoporphyrin IX-containing Hb. This basic purification method can be further followed by a sizing column (S-200), then another anion exchange column. Alternatively, this solution can be separated into molecular weight fractions using ion exchange chromatography according to the methods of the instant invention. The resulting solution can then be buffer exchanged to the desired formulation buffer.

The invention further provides nucleic acids encoding the novel polypeptides of the present invention. Those skilled in the art can readily derive a desired nucleotide sequence based on the knowledge of published nucleotide or amino acid sequences of known hemoglobin subunits with selection of codons and control elements specific for the organism used for expression, using methods known in the art. For example, the amino acid sequence of the dialpha domain and the beta domain of a synthetic hemoglobin can be used to derive the nucleic acids of the present invention, both of which are identified in FIG. 12 of PCT Publication WO 90/13645, incorporated herein by reference, with the following corrections to the nucleotide sequence: bases 55, 56 and 57 (codon 19) should read GCG and bases 208 and 209 (the first two bases of codon 70) should read GC. The following changes to the amino acid sequence of this figure would yield the pseudotetramer, rHb1.1: the gly-gly bridge at residues 142 and 143 of the dialpha domain can be changed to a single gly residue bridging $\alpha_1$ and $\alpha_2$ domains; residues 54 and 97 of the dialpha domain should read Gln; residue 70 of the beta subunit should read Asn; and residue 107 of the beta subunit should read Lys. The pseudotetramer, rHb1.1 is also described in Looker et al., *Nature*, 356:258–260 (1992), incorporated herein by reference.

The nucleic acids of the present invention can be used to construct plasmids to be inserted into appropriate recombinant host cells according to conventional methods or as described in the Examples below. Any suitable host cell can be used to express the novel polypeptides. Suitable host cells include, for example, bacterial, yeast, mammalian and insect cells. *E. coli* cells are particularly useful for expressing the novel polypeptides. Preferably, when multiple subunits are expressed in bacteria, it is desirable, but not required, that the subunits be co-expressed in the same cell polycistronically as described in WO 93/09143. The use of a single promoter is preferable in *E. coli* to drive the expression of the genes encoding the desired proteins.

The present invention is also directed to novel multimeric hemoglobin-like proteins containing at least three hemoglobin-like moieties, of which at least one is directly attached to the other moieties. The term "hemoglobin-like moiety" includes tetramers having four globin-like domains composed of two alpha domains and two beta domains and pseudomeric hemoglobin-like proteins as previously defined. The hemoglobin-like moiety that is directly attached to the other hemoglobin-like moieties is referred to herein as the "core hemoglobin-like moiety" or "core moiety" while the other hemoglobin-like moieties are referred to as the surrounding hemoglobin-like moieties" or "surrounding moieties."

In one embodiment, the core moiety is different from the surrounding hemoglobin-like moieties, which in turn can be the same or different from each other. Such multimeric hemoglobin-like proteins are referred to as heteromultimeric hemoglobin-like proteins (or heteromers). For example, the core moiety can be rHb1.1, while the surrounding moieties can be mutants referred to as K158C. The pseudotetramer, rHb1.1, is described in WO 90/13645, incorporated herein by reference. K158C is a mutant moiety of rHb1.1 and is composed of three polypeptides, one containing two alpha domains (a dialpha) and the other two each containing a single beta domain. A single lysine to cysteine substitution in the second alpha domain of the dialpha component appears at amino acid residue 158 of the K158C dialpha sequence. Note that because rHb1.1 consists of a dialpha molecule (two alpha subunits, each 141 amino acids in length, connected by a single glycine) mutations in the second subunit are denoted by the position with respect to the N terminus of the dialpha, and not the alpha subunit. Thus the mutation at position 158 is a mutation in the second alpha globin domain, corresponding to position 16 in normal alpha globin. A general method for obtaining a moiety having one or more asymmetrical cysteine mutations and the desirability of such asymmetrical crosslinked mutants are provided in WO 93/09143, which is specifically incorporated herein by reference. The publication also provides guidance for selecting other candidate sites for substitution on the alpha or beta domains.

The core and surrounding moieties can be directly attached by any means known in the art, including without limitation the use of chemical crosslinkers. Such linkers are discussed in Wang, S. S. (1993) *Chemistry of Protein Conjugation and Crosslinking*, CRC Press. Other suitable crosslinking methods are described, for example in Vandegriff, K. D.(1992) *Biotechnology and Genetic Engineering Reviews,* Volume 10: 404–453 M. P. Tombs, Editor, Intercept Ltd., Andover, England; and Winslow, R. M. (1992) *Hemoglobin-based Red Cell Substitutes,* The Johns Hopkins University Press, Baltimore 242 pp. Such crosslinking chemistries are generally linkers containing two or more functional groups. These functional groups can be the same or different (i.e., homobifunctional linkers, heterobifunctional linkers, homopolyfunctional linkers, or heteropolyfunctional linkers and can furthermore be dendrimeric, branched or contain armed cores) and include, for example, bis-imidoesters, bis-succinimidyl esters, oxidized ring structures of sugars or nucleotides, crosslinkers containing haloacetyl or vinyl sulfone functional groups, and dialdehyde and polyaldehyde crosslinkers, such as glycolaldehyde and glutaraldehyde.

For heteromultimeric hemoglobin-like proteins, a heterobifunctional chemical crosslinker is preferred, such as a succinimidyl 4-(N-maleimidomethyl) cyclohexane-1-carboxylate (SMCC) or N-γ- maleimidobutyrloxysuccinimide ester (GMBS). Preferably, the heterobifunctional chemical crosslinker is one that does not elicit a significant immunogenic response. Other useful heterobifunctional crosslinkers are described in WO 93/09143, incorporated herein by reference.

In tire case of GMBS or SMCC, for example, the succinimide of these compounds can be used to attach to the lysine residue of the non-cysteine mutated hemoglobin-like proteins, such as rHb1.1 (the core moiety). The maleimide can be used to attach to the cysteine of the hemoglobin-like protein containing a cysteine mutation, such as K158C. By first reacting linkers with the core moiety, then adding the desired amount of cysteine-containing mutant, various forms of these multimeric hemoglobin-like proteins can be made, for example a trimeric, tetrameric, pentameric and higher order multimeric proteins. Factors that constrain the number of hemoglobin-like moieties that can be attached to the core moiety include steric hindrance as additional surrounding moieties are added and the number of residues that are available for attaching to the crosslinkers. Methods for identifying and using such crosslinkers are known to those skilled in the art or as described in the Examples below.

In a further embodiment, the core moiety and the surrounding moieties can be the same moiety, which are referred to herein as "homomultimeric hemoglobin-like proteins." An example of a homomultimeric Hb-like protein is one which is composed of only K158C mutants.

For making the multimeric hemoglobin-like proteins of this embodiment, the formation of substantial amounts of polymerized proteins is preferably avoided. Polymerized proteins contain Hb-like moieties that are indirectly attached to the core moiety through attachment to an intervening hemoglobin-like moiety and are generally formed by uncontrolled crosslinking reactions. According to the methods of the instant invention, such random polymerization is reduced by coupling of specific reactive sites on the core hemoglobin protein to certain sites on the surrounding hemoglobin-like molecules. Any method known in the art can be used in which site specific attachment can be achieved.

The present invention also provides methods for making homomultimeric hemoglobin-like proteins, that is a multimeric hemoglobin-like protein composed of a core molecule that is the same as the surrounding molecules. These methods are accomplished by the use of a heterobifunctional crosslinker and a protective moiety, for example, borate. Alternatively, reaction conditions with any of the crosslinkers can be modified by altering for example, concentrations, temperatures or reaction time such that the degree of polymerization is constrained.

Through the use of an appropriate amine/sulfhydryl heterobifunctional crosslinker, a desired hemoglobin-like moiety, for example, rHb1.1, can be modified so that it will subsequently react with several rHb1.1 molecules bearing surface cysteine mutations as described in WO 93/09143. This reaction is achieved, for example, by first reacting the amine functionalities on unmodified rHb1.1 with the succinimide moiety of a heterobifunctional crosslinker in a sodium borate buffer at pH 8.5. Reaction with lysine residues on rHb1.1 leads to loss of the succinimide group of the heterobifunctional crosslinker by the formation of a stable amide linkage between the crosslinker and the hemoglobin. The unreacted maleimide residues of the heterobifunctional crosslinker are highly reactive towards sulfhydryl groups. The intrinsic sulfhydryl groups of rHb1.1 are prevented from reacting with the maleimide moiety of the heterobifunctional crosslinker by either their inaccessibility or by forming a complex with borate. After reaction with the succinimide group of the heterobifunctional crosslinker, the hemoglobin molecule can be considered to be "activated" at multiple surface lysine residues towards reaction with the surface sulfhydryl residue of, for example, a K158C hemoglobin mutant because the core moiety now has reactive maleimide residues attached to it.

By using an appropriate concentration of crosslinker and reaction time, which can be determined empirically by those skilled in the art, the reaction with surface cysteine-containing hemoglobin (e.g., K158C) with the activated core hemoglobin molecule yields higher molecular weight hemoglobins. The polymers that are formed by reaction of the activated hemoglobin and the cysteine-containing hemoglobin mutants have a distribution of apparent molecular weights. However, the distribution of molecular weights can be constrained to a certain extent by the extent of initial activation with the heterobifunctional crosslinker coupled with the use of certain moieties, such as, for example, K158C. The site-directed nature of the reaction with, for example, K158C limits the molecular weight distribution to predominantly pentameric hemoglobin. It is believed that the manipulation of reactivity, such as sulfhydryl reactivity, through formation of a reversible complex with a suitable protective buffer, such as borate/boric acid for certain mutants, is a novel method for controlling reactivity, such as sulfhydryl reactivity, in forming the multimeric hemoglobin-like proteins of the present invention.

Accordingly, the present invention further provides methods for making a multimeric hemoglobin-like protein. The methods are accomplished by:

(a) obtaining a first hemoglobin-like moiety having an amino acid capable of attaching to one end of a heterobifunctional linker to form a core hemoglobin-like moiety;

(b) obtaining at least two other hemoglobin-like moieties having an amino acid capable of attaching to the other end of the heterobifunctional linker;

(c) contacting the heterobifunctional linker to the first hemoglobin-like moiety to form a linked moiety; and (d) contacting the other hemoglobin-like moieties to the linked moiety to form the multimeric hemoglobin-like protein.

The invention further provides compositions containing the novel multimeric hemoglobin-like proteins of the present invention and the globin-like polypeptides, including proteins containing such polypeptides. In compositions containing the multimeric hemoglobin-like proteins, a polydisperse composition containing various multimeric proteins can be obtained, i.e., differing species of trimerics, tetramerics, pentamerics and so forth. In addition, these compositions containing the multimeric hemoglobin-like proteins are preferably substantially free of polymerized proteins, although they need not be completely free depending on the intended use of the desired proteins. As used in this context, "substantially free" means the presence of polymerized proteins will not adversely affect the desired function of the multimeric hemoglobin-like proteins. Furthermore, these multimeric hemoglobin-like proteins are substantially monodisperse. As used herein, "substantially monodisperse" means that there is less than 30% hemoglobin that is not the desired molecular weight. Accordingly, in a substantially monodisperse high molecular weight hemoglobin solution, less than 30% of the hemoglobin is not the target high molecular weight hemoglobin that is desired.

Note that the target monodisperse high molecular weight hemoglobin can comprise mixtures of high molecular weight, such as trimers, tetramers and pentamers. Likewise, in a substantially monodisperse pentahemoglobin solution, less than 30% of the hemoglobin in the solution is not pentahemoglobin. Preferably, a monodisperse high molecular weight hemoglobin solution contains less than 25% non-target hemoglobin, more preferably less than 20% non-target hemoglobin.

After crosslinking, regardless of crosslinking technology that is utilized, ion exchange chromatography is used to separate hemoglobin polymers by molecular weight according to the methods of the instant invention. Typically ion exchange chromatography is used to separate proteins according to differences in isoelectric point. Surprisingly, the inventors have found that ion exchange technology can be used to separate hemoglobins that have no measurable difference in isoelectric point. For example, the isoelectric point of rHb1.1 that has been crosslinked with glutaraldehyde is approximately 7.05 for mono-hemoglobin (1 tetramer) di-hemoglobin (2 tetramers), tri-hemoglobin, and higher order multimers. Nevertheless, such hemoglobins were resolved using the methods of the instant invention (see, for example, Example 12 herein).

According to the instant invention, the purification of the polydisperse hemoglobin solution is accomplished as follows. The polydisperse hemoglobin solution is transferred into a buffer compatible with the ion exchange matrix if required. A suitable buffer is, for example, 20 mM Tris, pH 8.0–8.9 at 8° C. The polydisperse hemoglobin solution is then loaded onto an ion exchange matrix. Such ion exchange matrices can be any suitable support, for example membranes or resins that are anion or cation exchange matrices. A particularly suitable exchange resin can be, for example, a Q-SEPHAROSE fast flow anion-exchange column (Pharmacia Biotech, Uppsala, Sweden). Alternate anion-exchange resins include, for example, Super Q 650 C or Toyopearl QAE-550C (TosoHaas Inc., Montgomery, Pa.) or Macro-Prep Q Support (Bio-Rad Inc., Hercules, Calif.). The amount of protein that can be loaded on the column can be varied depending on the binding capacity of the column and the mix of molecular weights desired. The flow rate of the column will depend on the type of column and resin used for the chromatography. Typically, for a 450 ml resin bed packed in an XK-50 column (Pharmacia Biotech, Uppsala, Sweden) a flow rate of 200 cm/hr is used.

After the column is loaded with the polydisperse hemoglobin solution, it is washed with sufficient column volumes of buffer to remove unbound protein from the column matrix. Such washes can be, for example, 2–3 column volumes (CV's) of 20 mM Tris buffer, pH 8.9 at 8° C. Alternatively, the column can be washed until the desired protein concentration in the eluent is reached. This can be determined by the absorbance at 215 or 280 nm, or by other suitable monitoring techniques. Next, the column is washed with the desired buffer system. This buffer system can include combinations of buffer, buffer concentrations and/or salt to elute the desired protein. Elution can occur utilizing any suitable elution scheme, for example by isocratic elution, stepwise isocratic elution, stepwise gradient elution or gradient elution. A particularly suitable elution scheme is by stepwise isocratic elution. Determination of suitable washes, elution buffers and elution schemes can be readily determined by one of skill in the art using the guidance provided herein.

For the purpose of removing glutaraldehyde crosslinked proteins with molecular weights <190 kDa the column can be washed with, for example, 11 CV's of 20 mM Tris buffer, pH 7.6 at 8° C. Using this system, the desired hemoglobin polymer fraction is then eluted with 20 mM Tris, pH 7.4 at 8° C. Likewise, monomeric hemoglobin can be removed from a pentahemoglobin solution formed using a polyfunctional crosslinker (see Example 18) using, for example, 7–8 CV wash 25 mM Bis-Tris/Tris pH=7.5 at 8° C. followed by elution with 25 mM Bis-Tris/Tris, 100 mM NaCl pH=7.5 at 8° C. The hemoglobin molecular weight fraction of interest can then formulated as desired, or further purified by, for example, ultrafiltration.

The hemoglobin-like proteins and compositions containing the globin-like polypeptides or the multimeric hemoglobin-like proteins (collectively "hemoglobins") can be used for in vitro or in vivo applications. Such in vitro applications include, for example, the delivery of oxygen by compositions of the instant invention for the enhancement of cell growth in cell culture by maintaining oxygen levels in vitro (DiSorbo and Reeves, PCT publication WO 94/22482, herein incorporated by reference). Moreover, the hemoglobins of the instant invention can be used to remove oxygen from solutions requiring the removal of oxygen (Bonaventura and Bonaventura, U.S. Pat. No. 4,343,715, incorporated herein by reference) and as reference standards for analytical assays and instrumentation (Chiang, U.S. Pat. No. 5,320,965, incorporated herein by reference) and other such in vitro applications known to those of skill in the art.

In a further embodiment, the hemoglobins of the present invention can be formulated for use in therapeutic applications. Example formulations suitable for the hemoglobin of the instant invention are described in Milne, et al., WO 95/14038 and Gerber et al., PCT/US95/10232, both herein incorporated by reference. Pharmaceutical compositions of the invention can be administered by, for example, subcutaneous, intravenous, or intramuscular injection, topical or oral administration, large volume parenteral solutions useful as blood substitutes, etc. Pharmaceutical compositions of the invention can be administered by any conventional means such as by oral or aerosol administration, by transdermal or mucus membrane adsorption, or by injection.

For example, the hemoglobins of the present invention can be used in compositions useful as substitutes for red blood cells in any application that red blood cells are used or for any application in which oxygen delivery is desired. Such hemoglobins of the instant invention formulated as red blood cell substitutes can be used for the treatment of hemorrhages, traumas and surgeries where blood volume is lost and either fluid volume or oxygen carrying capacity or both must be replaced. Moreover, because the hemoglobins of the instant invention can be made pharmaceutically acceptable, the hemoglobins of the instant invention can be used not only as blood substitutes that deliver oxygen but also as simple volume expanders that provide oncotic pressure due to the presence of the large hemoglobin protein molecule. In a further embodiment, the crosslinked hemoglobin of the instant invention can be used in situations where it is desirable to limit the extravasation or reduce the colloid osmotic pressure of the hemoglobin-based blood substitute. The hemoglobins of the present invention can be synthesized with a high molecular weight. Thus the hemoglobins of the instant invention can act to transport oxygen as a red blood cell substitute, while reducing the adverse effects that can be associated with excessive extravasation.

A typical dose of the hemoglobins of the instant invention as an oxygen delivery agent can be from 2 mg to 5 grams or more of extracellular hemoglobin per kilogram of patient body weight. Thus, a typical dose for a human patient might be from a few grams to over 350 grams. It will be appreciated that the unit content of active ingredients contained in an individual dose of each dosage form need not in itself constitute an effective amount since the necessary effective amount could be reached by administration of a plurality of administrations as injections, etc. The selection of dosage depends upon the dosage form utilized, the condition being treated, and the particular purpose to be achieved according to the determination of the skilled artisan in the field.

Administration of the hemoglobins of the instant invention can occur for a period of seconds to hours depending on the purpose of the hemoglobin usage. For example, as an oxygen delivery vehicle, the usual time course of administration is as rapid as possible; Typical infusion rates for hemoglobin solutions as blood replacements can be from about 100 ml to 3000 ml/hour.

In a futher embodiment, the hemoglobins of the instant invention can be used to treat anemia, both by providing additional oxygen carrying capacity in a patient that is suffering from anemia, and/or by stimulating hematopoiesis as described in PCT publication WO 95/24213. When used to stimulate hematopoiesis, administration rates can be slow because the dosage of hemoglobin is much smaller than dosages that can be required to treat hemorrhage. Therefore the hemoglobins of the instant invention can be used for applications requiring administration to a patient of high volumes of hemoglobin as well as in situations where only a small volume of the hemoglobin of the instant invention is administered.

Because the distribution in the vasculature of the hemoglobins of the instant invention is not limited by the size of the red blood cells, the hemoglobin of the present invention can be used to deliver oxygen to areas that red blood cells cannot penetrate. These areas can include any tissue areas that are located downstream of obstructions to red blood cell flow, such as areas downstream of thrombi, sickle cell occlusions, arterial occlusions, angioplasty balloons, surgical instrumentation, any tissues that are suffering from oxygen starvation or are hypoxic, and the like. Additionally, any types of tissue ischemia can be treated using the hemoglobins of the instant invention. Such tissue ischemias include, for example, stroke, emerging stroke, transient ischemic attacks, myocardial stunning and hibernation, acute or unstable angina, emerging angina, infarct, and the like. Because of the broad distribution in the body, the hemoglobins of the instant invention can also be used to deliver drugs and for in vivo imaging.

The hemoglobins of the instant invention can also be used as replacement for blood that is removed during surgical procedures where the patient's blood is removed and saved for reinfusion at the end of surgery or during recovery (acute normovolemic hemodilution or hemoaugmentation). In addition, the hemoglobins of the instant invention can be used to increase the amount of blood that can be predonated prior to surgery, by acting to replace some of the oxygen carrying capacity that is donated.

Under normal physiological conditions, nitric oxide is not produced in excess amounts. However, certain disease states are associated with excess nitric oxide production. Such conditions include septic shock and hypotension. In these cases, the crosslinked hemoglobin of the present invention can be used to remove excess nitric oxide from the vasculature or to remove any other ligand that is found in toxic excess and that can be bound to the hemoglobins of the instant invention.

The following Examples are intended to illustrate, but not limit, the present invention.

EXAMPLE 1

Production of Protein Solution Containing Modified Hemoglobin

A. Construction of a Bacterial System for the Production of Modified rHb1.1

On Jan. 20, 1994 *E. coli* strain SGE1661 was deposited with the American Type Culture Collection (ATCC Accession Number 55545). Note that Strain SGE1661 carrying the plasmid pSGE705 was denoted SGE1662. pSGE705 was a medium copy number plasmid because it resulted in approximately 100 copies of the plasmid per cell. The plasmids used in preparing pSGE705 are identified in Table 1, which also provides a brief description of each.

Materials. pBR322, pUC19 and pNEB193 were purchased from New England Biolabs, Beverly, Mass. Oligonudeotides were synthesized on an Applied Biosystems DNA Synthesizer Model 392. The oligonudeotides used in preparing pSGE705 are listed in Table 2. Restriction endonucleases were purchased from New England Biolabs (Beverly, Mass.) and used according to manufacturer's specifications. T4 DNA Ligase was purchased from either New England Biolabs or Gibco-BRL (Gaithersburg, Md.) and used according to manufacturer's specifications. Pfu polymerase was purchased from Stratagene (La Jolla, Calif.) and used according to manufacturer's specifications.

Media used to culture the strains are described in J. H. Miler, *Experiments in Molecular Genetics.* (Cold Spring Harbor Press 1972). and J. H. Miller, *A Short Course in Bacterial Genetics.* (Cold Spring Harbor Press 1992). Acridine orange, ampicillin and kanamycin sulfate were purchased from Sigma Chemical Co. (St Louis, Mo.). Tetracycline was purchased from Aldrich Chemicals (Milwaukee, Wis.).

TABLE 1

Plasmids

| PLASMID | DESCRIPTION |
|---|---|
| pSGE1.1E4 | rHb1.1 expression plasmid containing dialpha and beta genes |
| pSGE1.1E5 | like pSGE1.1E4 but ampicillin resistant instead of tetracycline resistant |
| pSGE490 | pUC19 lacI on a Bam HI-Hind III fragment |
| pSGE491 | pUC19 α on an Eco RI-Xba I fragment |
| pSGE492 | pNEB193 Ptac- α |
| pSGE493 | pUC19 β on an Xba I-Hind III fragment |
| pSGE500 | pUC19 α β on a Bam HI-Hind III fragment |
| pSGE504 | pSELECT-1 replace Sty I with a Pme I site |
| pSGE505 | pSGE504 rrnB T1 transcriptional terminator in the Eco RI-Cla I sites |
| pSGE507 | ColE1 ori and tet, 2213 bp |
| PSGE509 | ColE1 ori tet lacI, 3425 bp |
| pSGE513 | ColE1 ori tet lacI α β, 4386 bp |
| pSGE515 | ColE1 ori tet lacI diα β , 4812bp |
| pSGE700 | pTZ18U + diα β from pSGE515 |
| pSGE705 | modified rHb1.1 expression plasmid, ColE1 ori, tet, lacI, dialpha and beta genes |
| pTZ18U | a phagemid derivative of pUC19, for oligonucleotide directed mutagenesis |
| pDLII-91F | pGEM1 + α missing valine in 2nd position (Des-val) |
| pNEB193 | Like pUC19 but has more restriction sites in the multi cloning sites |
| pBRr322 | ColE1 ori tet amp |
| pRG1 | pACYC177 lacIq |

TABLE 2

Oligonucleotides

| OLIGO | SEQUENCE (5'-3') | DESCRIPTION |
|---|---|---|
| EV18 | CGGGAATACGGTCTAGATCATTAA | C-term of α gene, |
| SEQ. ID #4 | CGGTATTTCGAAGTCAGAACG | Xba I site |
| EV27 | GATCCGAGCTGTTGACAATTAATCATCGGCT | tac promoter |
| SEQ. ID #5 | CGTATAATGTGTGGAATTGTGACGGATAACAA TTTCACACAGGAAATTAATTAATGCTGTCTCC | sequence, Bam HI- Eag I sites |
| EV28 | GGCCGGAGACAGCATTAATTAATTTCCTGT | tac promoter |
| SEQ. D #6 | GTGAAATTGTTATCCGCTCACAATTCCACA CATTATACGAGCCGATGATTAATTGTCAAC AGCTCG | sequence, Bam HI- Eag I sites, complement of EV27 |
| EV29 | TCGGATTCGAATTCCAAGCTGTTGGATCCTTA | 5' end of α with Eco RI, |
| SEQ. ID #7 | GATTCAACTGTCTCCGGCCGATAAAACCACCG | Bam HI andEag I sites |
| EV30 | CGGAAGCCCAATCTAGAGGAAATAATATAT | 5' end of β with |
| SEQ. ID #8 | GCACCTGACTCCGGAAGAAAAATCC | Xba I site |
| EV31 | CCCGAAACCAAGCTTCATTAGTGA | 3' end of the β gene |
| SEQ. ID #9 | GCTAGCGCGTTAGCAACACC | with Hind III site |
| MW007 | TTTAAGCTTCATTAGTGGTATT | mutagenesis reverse primer |
| SEQ. ID #10 | TGTGAGCTAGCGCGT | replaces last 3 codons of β missing in pSGES15 |
| MW008 | CAGCATTAATTAACCTCCTTA | mutagenesis reverse |
| SEQ. ID #11 | GTGAAATTGTTATCCG | primer to optimize α ribozyme binding site (RBS) |
| MW009 | GGTGCATATATTTACCTCCTT | mutagenesis reverse primer |
| SEQ. ID #12 | ATCTAGATCATTAACGGTATTTCG | to optitize β RBS; remove 2nd Bgl II |
| TG14 | GGTTTAAACC | Pme I linker |
| SEQ. ID #13 | | |
| TG59 | GGCGAATAAAAGCTTGCGGCCGCG | Upstream of lacI gene, has |
| SEQ. ID #14 | TTGACACCATCGAATGGCGCAAAA CCTTTCGCGG- | Hind III and Not I site upstream of promoter |
| TG60 | GGGCAAATAGGATCCAAAAAAAAG | Downstream side of lacI |
| SEQ. ID #15 | CCCCCTCATTAGGCGGGCTTTAT CACTGCCCGCTTTCCAGTCGGG | gene with trp transcriptional terminator and Bam HI site |
| TG62 | CCCCGAAAAGGATCGAAGTA | upstream primer for pBR322 |
| SEQ. ID #16 | GCCCGCGGCCGCGTTCCACTG AGCGTCAGACCCC | ori positions 3170–3148 w/Bam HI and Not I site |
| TG63 | GGCGGTCCTGTITAAACGCT | downstream primer for |
| SEQ. ID #17 | GCGCTCGGTCGTTCGGCTGCGG | pBR322 ori positions 2380–2404 w/Pme I site |

Genetic and Molecular Biological Procedures. Standard bacterial genetic procedures are described in J. H. Miller, *Experiments in Molecular Genetics*, (Cold Spring Harbor Press 1972) and J. H. Miller, *A Short Course in Bacterial Genetics* (Cold Spring Harbor Press, 1992 ). Standard molecular biology procedures were performed as described in Sambrook et al., *Molecular Cloning*, (Cold Spring Harbor Press, 1989).

Plasmid DNA Transformation. DNA transformations were performed by the procedure described in Wensick et al., *Cell* 3: 315–325 (1974). Briefly, cells were grown to mid log phase and then pelleted, resuspended in an equal volume of 10 mM MgSO$_4$ and incubated on ice for 30 minutes. The cells were centrifuged and the pellet resuspended in ½ original volume of 50 mM CaCl$_2$ and placed on ice for 20 minutes. The cells were centrifuged again and then resuspended in 1/10 original volume of 50 mM CaCl$_2$. Plasmid DNA was added to the competent cells in a solution of 10 mM Tris-HCl pH 8.0, 10 mM MgCl$_2$ and 10 mM CaCl$_2$. The mixture was incubated on ice for 15 minutes and then incubated at 37° C. for 5 minutes. One milliliter of LB medium was added and the mixture incubated with shading for 30–60 minutes. The culture was then centrifuged, resuspended in 0.1 ml of LB medium and plated on the appropriate selective medium.

Purification of DNA. DNA fragments were purified from an agarose gel using the Geneclean system (Bio 101, Inc. La Jolla, Calif.) according to the method provided with product. PCR products were prepared and cleaved with restriction endonucleases using the Double Geneclean system. (Bio 101, Inc. La Jolla; method provided with product.) Briefly, the PCR product was purified away from the PCR primers, then the PCR product was cleaved with restriction endonuclease(s) and purified from the restriction endonuclease and buffer. The PCR product was then ready for a ligation reaction.

Annealing of oligonudeotides. Complementary oligonudeotides were annealed according to the following procedure. Equimolar amounts of each oligonucleotide were mixed in 15–25 μl of 10 mM Tris-HCl pH 8.0/1 mM EDTA and incubated at 65° C. for 30 minutes. The sample was transferred to a 37° C. water bath for 30 minutes. Finally, the sample was incubated on ice for 60 minutes or in the refrigerator overnight.

Oligonucleotide directed mutagenesis. Oligonucleotide directed mutagenesis was performed with the Muta-gene phagemid in vitro mutagenesis kit (Bio-Rad, Hercules, Calif.) according to manufacturer's instructions which are based on the method of Kunkel (Kunkel, T. A. (1985) *Proc. Natl. Acad. Sci. USA* 82: 488; Kunkel et al., (1987) *Methods Enzymol.* 154: 367). The rHb1.1 region of pSGE515 was cloned into pTZ18U (Bio-Rad, Hercules, Calif. or U.S. Biochemical, Cleveland, Ohio) on a BamHI-HindIII fragment to create pSGE700. Three oligonudeotides, MW007, MW008 and MW009 were used to simultaneously introduce multiple changes in a single reaction.

Preparation of pBR322 ori. PCR primers were designed to amplify the pBR322 origin of replication. These primers, TG62 and TG63, annealed to the positions 2380–2404 and 3170–3148 on the pBR322 DNA sequence (Sutcliffe, J. G. (1979) *Cold Spring Harbor Symp. Quant. Biol.* 43: 77–90). The PCR product was digested with NotI and PmeI. The DNA fragment was purified according to the Geneclean procedure.

Preparation of tet gene fragment. The source for the tet gene was pSELECT-1 (Promega Corp., Madison, Wis.). This plasmid has a number of restriction endonuclease sites, such as BamHI, HindIII, SalI and SphI removed from the tet gene (Lewis and Thompson (1993) Nucleic Adds Res. 18:3439–3443). A PmeI linker was inserted into the StyI site of pSELECT-1. This plasmid was designated pSGE504. Oligonucleotides TG71 and TG72 were annealed and ligated to the EcoRI-ClaI fragment of pSGE504. This plasmid, pSGE505, was shown to have the expected restriction endonuclease sites and to have lost the sites present in the multicloning site of pSELECT-1. pSGE505 was digested with NotI and PmeI. The 1417 bp fragment was purified according to the Geneclean protocol.

Preparation of lacI gene. The lacI gene was isolated by amplifying the gene sequence from pRG1 (Dana-Farber Cancer Inst, Boston) that carried the lacI gene. The PCR primers, TG59 and TG60 were designed to generate a wild type lacI promoter (Farabaugh, P. J. (1978) *Nature* 274:765), upstream of the gene and to place the trp terminator sequence (Christie et al., (1981) *Proc. Natl. Acad. Sci. USA* 78:4180–4184) downstream of the gene. The same step could be carried out using Y1089 (Promega) or chromosomal DNA from any *E. coli* strain carrying the lac region, such as MM294 (ATCC 33625.) The PCR product was gel purified and isolated according to the Geneclean procedure and cloned into BamHI-HindIII digested pUC19 DNA to make pSGE490.

Construction of pSGE515. PCR primers EV29 and EV18 were chosen to amplify the alpha gene from pDLII-91F (Hoffman et al., WO 90/13645). The purified PCR product was cleaved with the restriction endonucleases EagI and XbaI.

To create a plasmid that contained $P_{tac}$-α, the alpha gene (from above) and the tac promoter, which was prepared by annealing EV27 and EV28, were mixed with Eco RI-Xba I-cleaved pUC19 DNA. The mixture of the three DNA fragments, in approximately equimolar ratio, was treated with T4 DNA Ligase. After incubation the ligation mixture was used to transform SGE476 and ampicillin resistant transformants were selected. (Transformation into Strain MM294 (ATCC 33625) yields equivalent results.) An isolate with the correct restriction endonuclease fragments was designated pSGE492. The a gene and the tac promoter DNA sequences were verified by DNA sequencing.

Primers EV30 and EV31 were used to amplify the β gene from pSGE1.1E4 by PCR. The purified β gene fragment was digested with XbaI and HindIII and then mixed with XbaI-HindIII digested pUC19 DNA and treated with T4 DNA ligase. The ligation mixture was used to transform competent SGE476 (equivalent to MM294, ATCC 33625) and transformants were selected on LB+ampicillin (100 μg/ml) plates. An isolate that contained the appropriate restriction endonuclease fragments was chosen and designated pSGE493. The β gene was confirmed by DNA sequencing.

The β gene was isolated from pSGE493 by restriction with XbaI and HindIII followed by purification according to the Geneclean method. This DNA fragment was then ligated to XbaI-HindIII restricted pSGE492 DNA and transformed into SGE713. (Any dam⁻ strain such as JM110 (ATCC 47013) or GM119 (ATCC 53339) could also be used.) An ampicillin resistant transformant that carried a plasmid that had the appropriate restriction fragments was chosen and designated pUC19αβ (pSGE500).

The BamHI-Hind III fragment that contained the α and β genes of pSGE500 was purified according to the Geneclean method. An XhoI fragment that carried a portion of the di-α gene containing the glycine linker region was gel purified from pSGE1.1E5. pSGE1.1E5 (described in Hoffman et al., U.S. Ser. No. 789,179, filed Nov. 8, 1991) is a tetracycline sensitive analogue of pSGE1.1E4 (Hoffman et al., WO 90/13645), which could also have been used.

The pBR322 origin of replication region (pBR322 ori, above) was ligated to the tet gene fragment (above) and the ligation mixture was transformed into SGE476. (Transformation into MM294, above would yield equivalent results.) Tetracycline resistant transformants were selected and plasmid DNA was isolated and analyzed. An isolate that contained the appropriate restriction endonuclease fragments was chosen and designated pSGE507.

Next, pSGE507 and pSGE490 were digested with BamHI and NotI and the appropriate fragments were purified. The two purified fragments were ligated together and the ligation mixture was used to transform competent SGE713. (Any dam⁻ strain could also be used; see above.) Tetracycline resistant transformants were selected, and plasmid DNA was isolated and analyzed. A plasmid that had the appropriate restriction fragments was chosen and designated pSGE509.

The purified BamHI-HindIII fragment of pSGE500 that contained the α and β genes was ligated to BamHI-HindIII digested pSGE509. The ligation mixture was used to transform pSGE713 (see above for equivalent strains) and tetracycline resistant transformants were selected and characterized. An isolate yielding the correct size plasmid with the expected restriction endonuclease fragments was chosen and designated pSGE513.

The XhoI fragment of pSGE1.1E (described in Hoffman et al., U.S. Ser. No. 07/789,179, filed Nov. 8, 1991, now U.S. Pat. No. 5,545,727, incorporated herein by reference) that contained the di-α glycine linker sequence was ligated to XhoI digested pSGE513 to create a plasmid that contained the di-α gene. SGE753 was transformed with the ligation mixture and tetracycline resistant transformants were selected. (Transformation into SGE800 would have yielded equivalent results.) Isolates were screened to identify those that contained the XhoI fragment inserter into pSGE513 in the correct orientation. An isolate that contained the correct configuration of the di-α gene, as determined by restriction endonuclease analysis with EagI, was designated pSGE515.

Modification of pSGE515 to create pSGE705. The DNA sequence record used to design PCR primers for the amplification of the β gene did not contain the C-terminal three amino acids. Oligonucleotide directed mutagenesis was used to add these nine nucleotides to the DNA sequence of the β gene. In the same reactions, modifications were introduced to optimize the ribosome binding sites for the di-α and β genes, and to remove a BglII site near the end of the di-α gene. The HindIII-BamHI fragment from pSGE515 was subcloned into pTZ18U, creating pSGE700. pSGE700 was then used as a source of ssDNA for site-directed mutagenesis.

The following are the changes that were made with the oligonucleotides MW008 and MW009 to optimize ribosomal binding sites and to remove a BglI restriction endonuclease site.

```
di alpha
before - CAATTTCAC--AGGAAATTAATTAATGCTG       (SEQ. ID. NO. 25)
         ||||||||**||||**||||||||||||
after  - CAATTTCACTAAGGAGGTTAATTAATGCTG       (SEQ. ID. NO. 26)
```

Four nucleotide changes, shown above, including the insertion of two nucleotides, were introduced with MW008 to optimize the ribosome binding site for dialpha. (|-indicates identity, *-indicates a change)

```
beta
before - TAAaGATCTAGA---GGAAATAA-TATATGCAC    (SEQ. ID. NO. 27)
         |||*|||||||***|||**|||*|||||||||
after  - TAATGATCTAGATAAGGAGGTAAATATATGCAC    (SEQ. ID. NO. 28)
```

The six nucleotide changes shown above, including the insertion of four nucleotides, were introduced with MW009 to optimize the ribosome binding site for beta. The lower case "a" on the before strand was a T to A mutation in the construction of the alpha gene that introduced a Bgl II site into the sequence. This was removed so that there would only be a single Bgl II site in pSGE705. (|-indicates identity, *-indicates a change)

```
End of Beta
before - CTCGCTCAC---------TAATGAA  (SEQ.ID.NO.29)
         |||||||||*********|||||||
after  - CTCGCTCACAAATACCACTAATGAA  (SEQ.ID.NO.30)
```

MW007 introduced the coding sequence for the last three amino adds of the beta gene as shown above. (|-indicates identity, *-indicates a change)

Putative mutants were screened for loss of a BglII restriction endonuclease cleavage site (introduced by MW008). Seventeen of 24 had lost the site and were further characterized by DNA sequencing at the other two mutagenized sites. One of the 17 had incorporated all the modifications from the three oligonucleotides. These changes were verified by DNA sequencing and the rHb1.1 genes were cloned into BamHI-HindIII digested pSGE509. An isolate that had the correct restriction endonuclease fragments was designated pSGE705.

A new sequence upstream of the a gene minimized the distance between the tac promoter (De Boer et al., *Proc. Natl. Acad. Sci. USA* 80, 21–25, 1983) and the first codon of the alpha gene. The intergenic region between the di-α gene and the β gene was also designed to contain the minimum sequence that contained a restriction endonuclease site and the ribosome binding site for the β gene. A plasmid map of pSGE705 is shown in FIG. 1. The plasmid map indicates many of the restriction endonuclease cleavage sites. pSGE705 is smaller than its counterpart pSGE1.1E4, and the placement of its restriction sites facilitates modular alterations of the sequence. An unused antibiotic resistance marker was removed, and a promoter was added to the lacI gene that would allow tighter control of rHb1.1. expression. pSGE705 was the base plasmid used in all manipulations described in the Examples set forth below.

General Fermentation Protocol

Hemoglobin was expressed in the strains described herein using any one of the fermentation protocols described below. First, a fermentor inoculum was grown from seed stock. An optional 2 liter flask fermentation was then performed prior to transfer to a 15 liter fermentor and induction. Alternatively, 100 liter fermentations were used. If the latter approach was used, then a fermentor inoculum was grown from seed stock 2 liter shake flasks. Four of these shake flasks were then used to inoculate the 100 liter fermentors. The details of the fermentation process are described below.

Any suitable fermentation and pre-purification scheme (purification prior to the ion exchange molecular weight separation) can be used for the production of the material of the instant invention.

Seed Stock-All Fermentations

Seed stock was grown up in LB broth containing 10 g/L BactoTrypton™, 5 g/L yeast extract, 5 g/L NaCl, 0.2 g/L NaOH, and 10 ug/ml tetracycline to an optical density of 1.5–1.7 at 600 nm. The solution was then made up to 10% glycerol and stored at −80° C. until required.

15 Liter Fermentation Protocol

Fermentor Inoculum (500 ml broth in 2 L shake flasks-seed flasks)

To prepare the fermentor inoculum, seed stock was thawed and 0.1–0.4 ml of seed stock were inoculated into 500 ml of a solution (DM-1) containing approximately 4.1 g/L $KH_2PO_4$, 7 g/L $K_2HPO_4$, 2 g/L $(NH_4)_2SO_4$, 1 g/L $Na_3$ citrate-$2H_2O$, 153 mg/L $MgSO_4.7H_2O$, 2.3 g/L of L-proline, 2 g/L yeast extract, 4.8–5.5 g/L glucose, 320 mg/L thiamine HCl, 10 mg/L tetracycline, and 3 ml/L of a trace metal solution containing 32.5 mg/L $FeCl_3.6H_2O$, 1.6 mg/L $ZnCl_2$, 2.4 mg/L $CoCl_2.6H_2O$, 2.4 mg/L $Na_2MoO_4.2H_2O$, 1.2 mg/L $CaCl_2.2H_2O$, 1.5 mg/L $Cu(II)SO_4.5H_2O$, 0.06 mg/L $H_3BO_3$, and 120.2 ml/L HCl. This culture is allowed to grow for 8–10 hours at 37° C. on a shaker. Two flasks were combined and used to inoculate the 15L fermentors if no intermediate "2 Liter" fermentation was performed. Alternatively, an intermediate seed fermentation in two liter fermentors was performed prior to the 15 liter fermentation.

Fermentor (2 L volume-seed fermentation) As an optional intermediate step, the cells were grown in a 2 liter fermentation. 400 mL of the seed fermentation was then aseptically transferred to a 2-liter New Brunswick fermentor containing approximately 1700 mL of a solution containing approximately: 2.2 g/L $KH_2PO_4$, 4 g/L $K_2HPO_4$ and 2.2 g/L $(NH_4)_2SO_4$.

The medium in the fermenter also contained: 1.2 g/L trisodium citrate, 1.2 g/L $MgSO_4.7H_2O$, 2.5 g/L proline, 3.1 g/L of the trace metal solution described above, 0.1 mg/L tetracycline in 50% ethanol solution, 345 mg/ L thiamine HCl in purified water, sterile filtered solution, 200 g/L of 70% glucose, 50+10 g/L of 30% $NH_4OH$, and 2 ml PPG 2000 (polyethylene glycol 2000).

Cells were grown in the fermentor for approximately 10 hours. The pH was maintained at 6.8–6.95 by addition of 15% to 30% $NH_4OH$, dissolved oxygen was maintained at or above 20%, and 50–70% glucose was added throughout the growth period, sufficient to maintain low but adequate levels of glucose in the culture (2 g/L-10 g/L). The culture was grown at approximately 30° C. to an $OD_{600}$~2–5.

15L Fermentor (14 L volume in 20 L Fermentor-"15L")

Either 800 mls of the seed flask or 400 mls of the "2 liter" seed fermentor were then aseptically transferred to a 20-liter fermentor containing 8 liters of the following media (DM-4-RP): 1.3 g/L $KH_2PO_4$, 2.4 g/L $K_2HPO_4$, 1.3 g/L $(NH_4)_2SO_4$, 195 mg/L thiamine HCl, 6.1 mg/L tetracycline, 1.8 g/L proline, and 2.2 ml/L of the trace metal solution described above. Note that masses of added reagents are calculated using the final volume of fermentation (11.5 liters) and are approximate within measurement error. The pH was maintained at 6.8 to 6.95 by addition of 15% to 30% $NH_4OH$, dissolved oxygen was maintained at or above 20%, and 50 to 70% glucose was added throughout the growth period, sufficient to maintain low but adequate levels of glucose in the culture (2 g/L-10 g/L). Dissolved oxygen was maintained as dose to 20% as possible. The culture was grown between 28 and 32° C. until an $OD_{600}$ of 30 was reached. Induction was accomplished by the addition of 10–1000 μM isopropyl thiogalactoside (IPTG). Upon induction of hemoglobin synthesis, the E. coli heme biosynthesis was supplemented by addition of hemin dissolved in 1 N NaOH, either by addition at induction of the total mass of hemin required, by continuous addition of hemin throughout the induction period, or by periodic addition of hemin dissolved in 50 mM to 1 M NaOH (e.g. one third of the total mass of hemin to be added to the fermentor was added at induction, another third was added after ¼ of the total time after fermentation had elapsed, and the last third was added half-way through the induction period). Total hemin added ranged from 50 to 300 mg/L. The fermentor was allowed to continue for 8–12 hours post-induction.

100 Liter Fermentation Protocol

Fermentor Inoculum (500 mL broth in 2 L shake flasks)

To prepare the fermentor inoculum, seed stock was thawed. Seed stock (100 ml) was grown up in 500 ml of DM59 in an Erlenmeyer flask at 37° C. in a 1 inch rotary shaker (275 to 300 rpm) for 8 to 10 hours. DM59 media is: 3.34 g/L $KH_2PO_4$, 5.99 g/L $K_2HPO_4$, 1.36 g/L $NaH_2PO_4.H_2O$, 1.95 g/L Na2HPO4, and 1.85 g/L $(NH_4)SO_4$ which are sterilized. After sterilization, 12.20 ml/L of a trace metal solution was added. The trace metal solution contained: 134.2 g/L tripotassium citrate, 32.2 g/L trisodium citrate, 27 g/L $FeCl_3.6H_2O$, 2.2 g/L $ZnCl_2$, 0.3 g/L $CoCl_2.6H_2O$, 0.3 g/L $Na_2MoO_4.2H_2O$, 2.73 g/L $MnCl_2$, 6.6 g/L $CaCl_2.2H_2O$, 1.5 g/L $Cu(II)SO_4.5H_2$ O, and 15 ml/L 85% $H_3PO_4$. In addition, the following components were added to the media after sterilization to achieve the final concentrations indicated: 10 mg/L tetracycline and 320 mg/L thiamine. Polypropylene glycol 2000 was added if a foaming problem was observed.

Fermentor (100 L volume)

2000 mL of the Fermentor Inoculum was then aseptically transferred to a 100-liter BioLafitte fermentor containing 54 L of DM59 medium described above.

The fermentor was run at 30±1° C., controlling dissolved oxygen at 20% and glucose between 0–6 g/L. At OD 30±2, induction occurred by lowering the temperature of the fermentor to 26° C., adding 43.5 mL of 100 mM IPTG and 73 mL of 50 mg/mL hemin. At 3 hours post induction, 96 mL of 50 mg/mL hemin was added, at 6 hours post induction, 125 mL of 50 mg/mL hemin was added, at 9 hours post induction, 125 mL of 50 mg/mL hemin was added and at 12 hours post induction, 125 mL of 50 mg/mL hemin was added. Harvest and further purification occurred at 16 hours post induction. Cells were either immediately purified or frozen for later purification.

Purification

If required, frozen cells were partially thawed in warm water for approximately 20–30 minutes. Cells were chopped into small bits in a steel beaker using break buffer (40 mM Tris base, 1 mM benzamidine) as needed. The chopped cells and break buffer at a ratio of 2 mL break buffer per 1 gram of frozen cells were placed in a Waring Industrial Blender and homogenized for 1–5 minutes on the low setting. The solution was allowed to settle for 5 minutes after homogenization and any foamed material was removed.

A Niro Panda™ cell disruption device (Niro Hudson, Inc. Hudson, Wis.) was prepared for homogenization by passing 200–300 mL of break buffer through the system. Cells were lysed by one or two passages of the homogenized cell solution through the Niro set at 850 bar. The pH of the lysate was adjusted to approximately 8 with sodium hydroxide, and sufficient $Zn(OAc)_2$ was added to make the solution 2–4 mM in $Zn(OAc)_2$. The solution was then spun at 10,000 rpm in a JA-10 rotor at 4° C. for 60 minutes in a Beckman centrifuge. The supernatant was collected and was optionally diluted 1:1 with distilled water. When using this protocol to purify K158, care should be taken to keep levels of oxygen as low as possible.

Chromatography

All solutions were 4° C. and were adjusted to the correct pH at 4° C. 500 mL of Chelating SEPHAROSE fast flow resin (Pharmacia, Piscataway, N.J.) was prepared by washing with 4 column volumes of distilled water. Flow through the column for all steps was 200 mL/min. The resin was charged with 2 to 3 column volumes of 2 mM $Zn(OAc)_2$ followed by 2–3 column volumes of 200 mM NaCl. The lysate was loaded onto the column and washed with 4 to 6 column volumes of 20 mM Tris, 500 mM NaCl, pH 8.5, 7–8 column volumes of 240 mM Tris, pH 8.5, and 7–8 column volumes of 20 mM Tris, pH 8.5. Hemoglobin was eluted with 15 mM EDTA, 20 mM Tris, pH 8.5 and collected into 200 mL of well oxygenated 20 mM Tris, pH 8.5. The column was then rinsed with an additional 3–4 column volumes of 15 mM EDTA, 20 mM Tris, pH 8.5, regenerated with 4 column volumes of 200 mM NaCl and stored in 0.2 N NaOH.

The solution was then buffer exchanged 5 times into 20 mM Tris, pH 8.5 prior to loading onto 200 mL of a SEPHAROSE Q column. The column had been prepared by rinsing with 4 column volumes of distilled water, 4 column volumes of 1 M NaCl, 4 additional column volumes of distilled water and equilibrating with 3 to 4 column volumes of 20 mM Tris, pH 8.5. After loading the sample, the column was washed with 2 to 3 column volumes of 20 mM Tris, pH 8.5 and eluted with 20 mM Tris, pH 7.6. Fractions were collected and pooled if the $A_{575}/A_{540}$ ratio was greater than or equal to 1.03. The column was then cleaned with 3–4 column volumes of 1 M NaCl, 4 column volumes of distilled water, 2–3 column volumes of 50% acetic add, 4 column volumes of distilled water and finally 2–3 column volumes of 0.2 N NaOH for storage. The column was run at 30 mL/min flow rate. The resultant hemoglobin was stored at −80° C. or in liquid nitrogen.

EXAMPLE 2

Construction of Di-dialpha Gene Construct Linked by a 7 Amino Acid Linker (SGE 939)

A. Construction of pTZ19U/705 Mutants rHb1.1 genes were cloned as a BamHI/HindIII DNA fragment into pTZ19U (BioRad, Hercules, Calif.). This construct was then transformed using a modified process of the Hanahan protocol (Hanahan, *J. Mol. Biol.*, 166:557

(1983)) into CJ236 E. coli strain (BioRad). The Hanahan transformation buffer contained 45 mM MnCl$_2$, 60 mM CaCl$_2$, 40 mM KOAc, 620 mM sucrose, 15% glycerol and 100 mM rubidium chloride. A 5 ml culture of an E. coli strain was started in 2× TY broth from an isolated colony and cultured overnight. Then, 200 ml of 2× TY broth was inoculated with 2 ml of the overnight culture and incubated at 37° C. with vigorous shaking for 2.5 hours. The culture was then transferred to two 300 ml centrifuge tubes and placed on ice for 15 minutes. Cells were pelleted in a centrifuge at 8000 rpm, 4° C., for 10 minutes and the supernatant was poured off. The cells were gently but thoroughly resuspended in 80 ml transformation buffer. The cells were again pelleted at 8000 rpm, 10 minutes at 4° C. The cells were gently resuspended in 20 ml of ice-cold transformation buffer and left on ice for 30–60 minutes. Cells were aliquoted in buffer into twenty 1 ml tubes. The cells were quickly frozen on dry ice and stored at −80° C.

Single-stranded DNA containing uracil substitutions was isolated and oligonucleotide-directed mutagenesis was performed using the Muta-gene Kit (BioRad, Hercules, Calif.) and standard protocols according to the manufacturer's instructions. Two pTZ19U/705 clones were prepared as follows.

The first pTZ19U/705 clone was prepared using oligonucleotide JD29 (ACC GTT CTG ACT AGT AAA TAC CGT TAA TGA [SEQ. ID. NO. 18]). This oligonucleotide created a unique SpeI site in the end of the dialpha domains. A second pTZ19U/705 done was prepared using oligonudeotides JD28 (5'-GGA GGT TAA TTA ATG CTG TCT CCT GCA GAT-3' [SEQ. ID. NO. 19]) and JD30 (5'-CTG GTG GGT AAA GTT CTG GTT TGC GTT CTG-3' [SEQ. ID. NO. 20]). The resulting clone incorporated a unique PstI site in the dialpha genes and removed an SpeI site in the beta domain.

B. Assembly of the Di-dialpha Gene Construct

The assembly of di-dialpha gene construct was accomplished by removal of a dialpha gene cassette from the first pTZ19U/705 clone using BamHI/SpeI enzymes and gel purification of the DNA fragment. A second pTZ19U/705 clone was cut with PstI/BglII enzymes to give a second dialpha gene cassette with the 5' end of the beta gene, which was also purified. These were then further ligated together with annealed oligonudeotides JA113 and JA114 to create a di-dialpha cassette with a 7 amino acid fusion peptide linker linking the two dialpha globins.

(SEQ.ID.NO.2)
GlyGlySerGlyGlySerGlyGlySerGlyGlySerGlyGly pSGE1008 was created in the same fashion as pSGE1006, except that the replacement linker was a 16 amino add linker of the following sequence:

(SEQ.ID.NO.3)
SerGlyGlySerGlyGlySerGlyGlySerGlyGlySerGlyGlySer

EXAMPLE 3

Construction of a High Copy Plasmid

The construction of pSGE720 was performed in two stages. First, the pUC origin of replication was introduced to create plasmid pSGE715, which is similar to pSGE705 in that it includes the lacI gene. Then, the lacI gene was deleted from the plasmid and replaced with a short oligonucleotide containing several convenient restriction sites to create plasmid pSGE720.

A. Construction of pSGE715

The pUC origin of replication was introduced to create plasmid pSGE715 through pSGE508, which is identical to pSGE509 with the exception of a single basepair substitution at base 602 (G→A). The substitution changes the pBR322 origin of replication to a pUC19 origin of replication.

Plasmids pSGE508 and pSGE705 were digested to completion with restriction enzymes BamHI and HindIII, according to the manufacturer's instructions (New England Biolabs.). The plasmid, pSGE508, was digested first with BamHI to completion, then HindIII was added, and the digestion continued. The pSGE705 digest was purified with Promega Magic DNA Clean-up protocols and reagents (Promega, Madison, Wis.) and further digested to completion with BglI, according to the manufacturer's instructions (New England Biolabs). The enzymes in both pSGE508 and pSGE705 digests were inactivated by heating at 67° C. for 10 minutes, then the DNA was pooled and purified together using Promega Magic DNA Clean-up protocols and reagents. The DNA was suspended in ligation buffer, T4 DNA ligase was added to one aliquot, and the DNA was incubated overnight at 16° C. SGE1661 cells were made competent by the method of Hanahan, using rubidium

```
JA113: 5'-CT AGT AAA TAC CGA TCG GGT GGC TCT GGC GGT TCT GTT CTG TCT CCT GCA-3'    (SEQ.ID.NO.21).

JA114: 5'-GG AGA CAG AAC AGA ACC GCC AGA GCC ACC CGA TCG GTA TTT A-3'             (SEQ.ID.NO.22).
```

This di-dialpha cassette was then ligated as a BamHI/BglII fragment into pSGE705 (described in PCT publication number WO 95/14038, herein incorporated by reference) that had the rHb1.1 genes removed as a BamHI/BglII fragment. The resulting di-dialpha plasmid (pSGE1000) was transformed into SGE1661 (also described in PCT publication number WO 95/14038) using the modified Hanahan's protocol described above to create SGE939. Two other plasmids were also constructed using the same methods described above, pSGE1006 and pSGE1008. pSGE1006 corresponds to pSGE1000, except that the linker linking the two dialpha regions was excised as an SpeI/PstI fragment and replaced with a synthesized region encoding a 14 amino add linker of the following sequence:

chloride (Hanahan, D., In *DNA Cloning; A Practical Approach* (Glover, D. M., ed.) vol. 1, pp.109–135, IRL Press, Oxford, 1985), and transformed with the ligation mix according to the Hanahan protocol. Transformants were selected by plating the cells on LB plates containing 15 μg/ml tetracycline. Candidates were screened by restriction digestion to determine the presence of the rHb1.1 genes, and sequencing to detect the pUC origin of replication. Several candidates were identified, and the resulting plasmid was named pSGE715, and pSGE715 in SGE1661 was called SGE1453.

The copy number of pSGE715 is about four-fold higher than pSGE705, measured to be about 460 plasmids per cell. As noted above, the difference between pSGE705 and pSGE715 is a single basepair change in the origin of replication region, which has been confirmed by sequencing.

B. Construction of pSGE720

The lacI gene was deleted from pSGE715, replacing it with a short oligonucleotide containing several convenient restriction sites, by the following steps. First, plasmid pSGE715 was digested to completion with restriction enzymes BamHI and NotI, according to the manufacturer's instructions (New England Biolabs). The pSGE715 digest was purified with Promega Magic DNA Clean-up protocols and reagents. The DNA was mixed with annealed, kinased oligonucleotides, CBG17+CBG18, and suspended in ligation buffer.

```
CBG17 = 5'-GGCCGCCTTAAGTACCCGGGTTTCTGCAGAAAGCCCGCCTA    (SEQ.ID.NO.: 23)
ATGAGCGGGCTTTTTTTTCCTTAGGG-3'

CBG18 = 5'-GATCCCCTAAGGAAAAAAAAGCCCGCTCATTAGGCGGGCTTT    (SEQ.ID.NO.: 24)
CTGCAGAAACCCGGGTACTTAAGGC-3'
```

T4 DNA ligase was added to one aliquot, and the DNA was incubated overnight at 16° C. SGE1821 cells were made competent by the method of Hanahan, using Rubidium Chloride, and transformed with the ligation mix according to the Hanahan protocol. SGE1821 contains pRG1 plasmids in addition to pSGE720. pRG1 is a low copy number plasmid containing LacIq. Transformants were selected by plating the cells on LB plates containing 15 g/ml tetracycline. Candidates were screened by restriction digestion using PstI and SmaI to detect the presence of the new linker and the absence of the lacI gene, and sequenced to detect the pUC origin of replication and the absence of the lacI gene. Several candidates were identified, and the resulting plasmid was named pSGE720. The plasmid, pSGE720 in SGE1675 was denoted SGE1464.

EXAMPLE 4

High Copy Di-dialpha Construct

A second plasmid containing the di-dialpha hemoglobin genes was created using pSGE720 as the vector. The di-dialpha gene cassette was removed as a BamHI/HindIII fragment and gel purified. The vector pSGE720 was also cut with BamHI/HindIII and the rHb1.1 genes removed. The vector was gel purified. The di-dialpha cassette was ligated into the pSGE720 vector, resulting in a new vector pSGE1004. This new vector was then transformed into E. coli strain SGE1675 using the modified Hanahan method as described below to produce strain SGE946.

EXAMPLE 5

Characterization of SGE939 and SGE946 Globins

Several 15 liter fermentations were performed on both strains SGE939 and SGE946 and soluble vs. insoluble western blots were performed using conventional methods. This data coupled with purification yields indicated that more soluble protein could be obtained from SGE946 (250–300 mg/L by the BioCAD assay (BioRad). The data obtained shows that both strains make di-dialpha globin and beta globin proteins, but that the SGE946 strain makes a larger amount of total protein and soluble protein.

The SGE939 hemoglobin-like protein was first eluted from a Q-SEPHAROSE column and then from a S-SEPHAROSE column on an FPLC. Fractions were collected by eluting with a pH gradient. By SDS-PAGE analysis, there appeared to be a population of degradation products since these cross-reacted with anti-rHb antibodies. The cleanest fractions were pooled and analyzed by C4 HPLC. A chromatogram of SGE939 showed the beta globin eluting at 43.7 minutes as expected, and the di-dialpha peak eluting at 61.8 minutes. Dialpha globin normally eluted at about 55 minutes under these conditions. There was also a peak at 56.2 minutes and a large shoulder on the di-dialpha peak. The peaks were collected and analyzed by mass spectroscopy. The beta globin peak gave the expected molecular weight of 15,910 daltons, while the di-dialpha peak gave a molecular weight of 61,088 daltons. The calculated molecular weight for beta globin is 15,913, while the calculated molecular weight of di-dialpha globin is 61,107.8 daltons. These results indicate that the protein expressed from SGE939 contained the expected di-dialpha polypeptide. The protoporphyrin IX content was shown to be below 3%. The $P_{50}$ averaged to be 24.7 and the $n_{max}$ was 1.75.

EXAMPLE 6

Tetra-Dialpha

A. Construction of Di-dialpha Vector Containing the K158C Mutation

Replacing the lysine residue at position 158 of dialpha globin allows chemical cross-linking of rHb1.1 molecules to form a dimeric hemoglobin molecule referred to as K158C. This mutation can be inserted into the di-dialpha expression plasmid (pSGE1000), to produce a mutant genetically linked di-hemoglobin that can be chemically cross-linked to form a tetra-hemoglobin. The modification will place the K158C mutation in the fourth (3'-terminal) alpha globin coding sequence of the di-dialpha plasmid. The K158C mutation is a 3 base change in the coding sequence, and can be transferred among dialpha-containing vectors on an Eag I-Bgl II restriction fragment. Because there are multiple Eag I sites in pSGE1000, an intermediate cloning step in the plasmid "pFusion II" is required. The cloning steps are as follows:

1. Isolate an EagI-Bgl II fragment containing the K158C mutation from pSGE1.1E4
2. Isolate large Eag I-Bgl II fragment from plasmid pFusion II, which removes the comparable "wild type" fragment from the second alpha gene
3. Ligate above fragments to form the intermediate pFusion II-based vector containing the K158C mutation
4. Replace the Pst I-Bgl II fragment in pSGE1000 with the Pst I-Bgl II fragment containing the K158C mutation.

B. Development of a Cloning Strategy for Genetically Linked Tetra Dialpha

Expression of a genetically linked tetra-hemoglobin molecule requires construction of a plasmid containing coding sequences for four dialpha hemoglobin genes, connected by coding sequences for peptide linkers, and one beta globin gene. A plasmid with these characteristics can be based on pSGE1000, which is currently being used to express a genetically linked di-hemoglobin. The following steps will be required to generate this plasmid:

1. Generate a modified vector with a new restriction site at the 5' end of the di-dialpha coding sequence;
2. Generate a second modified vector with a new restriction site at the 3' end of the di-dialpha coding sequence;
3. Design an amino acid sequence suitable for linking the di-dialpha molecules in such a way that a tetra-hemoglobin can assemble and design the DNA sequence required to encode the peptide linker; and
4. Assemble a new plasmid containing the two modified di-dialpha sequences, the linker sequence, and either a 705 or 720 plasmid background.

Silent mutations in were identified in the di-dialpha sequence that will generate restriction sites unique to di-dialpha in either the 705 or 720 (low and high-copy) plasmid backgrounds, near the 5' and 3' ends of the di-dialpha coding sequence. A restriction site for one of the enzymes, AatII, is also present in the beta globin gene; the site in the beta gene will be removed to facilitate cloning. A preliminary cloning strategy has been generated for construction of a tetra-hemoglobin expression vector as follows:
1. Create an Aat II site at the 3' end of a dialpha gene in pFusion II by site directed mutagenesis to create a fragment denoted "A1."
2. Subclone A1 into di-dialpha on a PstII BglII restriction fragment to create "A2."
3. Remove the AatII site from the beta globin gene in pFusion II by site directed mutagenesis to create "B1."
4. Subclone "B1" into a second di-dialpha construction on a PstI/BglII fragment to create "B2."
5. Create a B1pI site at the 5'end of the dialpha gene in pFusion I by site directed mutagenesis to create "C1."
6. Subclone C1 on a BamHI/Spe I fragment into the modified di-dialpha plasmid (B2) to create "D1."
7. Isolate the BamHI/AatII fragment from A2, and the B1pI/HindIII fragment from D1; ligate with a new synthetic sequence encoding a peptide linker containing AatII and B1PI ends, in a convenient plasmid background to form a tetrahemoglobin coding sequence.

EXAMPLE 7

General Transformation Procedure

A modified Hanahan protocol was used to produce competent *E. coli* cells. The Hanahan Transformation buffer contains 45 mM $MnCl_2$, 60 mM $CaCl_2$, 40 mM KOAc, 620 mM sucrose, 15% glycerol and 100 mM rubidium chloride. A 5 ml culture of an *E. coli* strain was started in 2× TY broth from an isolated colony and cultured overnight Then, 200 ml of 2× TY broth was inoculated with 2 ml of the overnight culture and incubated at 37° C. with vigorous shaking for 2.5 hours. The culture was then transferred to two 300 ml centrifuge tubes and placed on ice for 15 minutes. Cells were pelleted in a centrifuge at 8000 rpm's, 4° C., for 10 minutes and the supernatant was poured off. The cells were resuspended gently, but thoroughly in 80 ml transformation buffer. The cells were again pelleted at 8000 rpm for 10 minutes at 4° C. The cells were gently resuspended in 20 ml of ice-cold transformation buffer and left on ice for 30–60 minutes. Cells were aliquoted in buffer into twenty 1 ml tubes. The cells were quickly frozen on dry ice and stored at −80° C.

EXAMPLE 8

Preparation of BMH-crosslinked di-alphaK158C (Di-hemoglobin)

Di-hemoglobin was produced by crosslinking dialpha hemoglobin containing a K158C mutation in the second alpha globin domain using bismaleimidohexane (BMH, Pierce Chemical Co., Rockford, Ill.). BMH is a homobifunctional maleimide crosslinker, and its primary reactivity is towards sulfhydryl residues. The linkage is irreversible once formed. The alkane spacer between the maleimide residues is hexane (six carbons) and the molecule has poor solubility in buffered aqueous solutions. The nominal length of the crosslinker is 16.1 Å.

K158C was concentrated to 60 mg/mL in 20 mM Tris buffer pH 8, and deoxygenated by gas exchange with humid oxygen free nitrogen in a rotating glass flask (ROTOVAP RE111, Brinkmann, Inc., Cuntiague Road, Westbury, N.Y.). K158C was maintained in the deoxy form in order to limit the reaction of BMH with the intrinsic sulfhydryls of hemoglobin, especially residue Cys93 in the beta subunit. The reactivity of this residue with sulfhydryl reactive reagents is generally at least 50 fold slower in the deoxy form than in liganded forms of hemoglobin. The reactivity of the surface K158C residue is not affected significantly by the heme ligation state.

A solution of BMH was prepared in pure dimethyl sulfoxide (DMSO) at 10 mg/mL. An aliquot of this solution was added to the deoxyHb solution (0.6 moles of BMH per mole of Hb, maintaining deoxy conditions) with swirling to mix, and the sample was allowed to react for 1 hour on ice. Following reaction, the hemoglobin solution was centrifuged or filtered (0.2 micron) to remove any precipitated material, diluted to 25 mg/mL and then chromatographed on SEPHACRYL S-200 HR (Pharmacia, Uppsala, Sweden) to resolve the dihemoglobin fraction from the unreacted mono-hemoglobin and the small amount of trihemoglobin formed during the reaction. Two S-200 HR columns (Pharmacia BPP 113, ca. 6L of resin each, 11.3 cm diameter×60 cm) were used in series to give acceptable resolution and volume handling capabilities. The yield of coupling was typically 60%, and about 50% of the starting hemoglobin was recovered following size exclusion chromatography. Following chromatography on Q-SEPHAROSE to remove endotoxin, the dihemoglobin was submitted for several routine analyses and the results are reported below. Methods for these analyses are described in PCT publication WO 95/14038. Average molecular weight was determined by size exclusion chromatography using a SUPEROSE 12 column using Bio-Rad molecular weight standards (Bio-Rad, Hercules, Calif.).

| Assay | Result |
| --- | --- |
| Endotoxin (LAL assay) | 0.6 EU/mL |
| *E. coli* protein | below detection |
| Protoporphyrin IX | 1.14% |
| p50, Torr at 37° C. | 32.7 |
| Nmax. | 2.09 |
| Average molecular weight | 128 kDa |

EXAMPLE 9

LAL Assay for Endotoxin

Fifty microliters of endotoxin standard, blank diluent, or hemoglobin solution (rHb1.1) was mixed with 50 ul of LAL lysate (BioWhittaker, Inc., Walkersville, Md.) in a well of a 96-well, pyrogen-free microtiter plate, according to the manufacturer's instructions. The mixture was allowed to incubate for 30 minutes in a 37° C. water bath. One hundred microliters of acetate-Ile-Glu-Gly-Arg-(SEQ ID. NO.25) conjugated to para-nitroaniline (chromogenic substrate) was added to each well and the plate allowed to incubate for an additional 16 to 60 minutes at 37° C. The reaction was stopped by the addition of 50 ul 25% glacial acetic acid, and the samples transferred to HPLC sample vials for analysis.

Twenty microliters of each sample was injected onto a Vydac C4-reversed phase chromatography column (2 mm×250 mm), pre-equilibrated at 40° C., 5% Solvent B. (Solvent A is 20% acetonitrile in water with 0.1% TFA and Solvent B is 100% acetonitrile with 0.1% TEA). The chromatographic system was run at a flow of 1 ml/min. Separation was achieved as follows: a 1 minute hold in 95% Solvent A/5% Solvent B after injection, a 4 minute ramp to 50% Solvent A/50% Solvent B, a 2 minute increase to 100% Solvent B, a 3 minute wash in 100% Solvent B, a return to 95% Solvent A/5% Solvent B over 1 minute and an equilibration at 95% Solvent A/5% Solvent B for 4 minutes. The separation was monitored at 405 nm.

The peak areas of the standard solutions were used to construct a standard curve against which test samples were measured. A series of curves were generated from the analysis of standard solutions ranging in concentrations from 0.5 EU/ml to 0.0005 EU/ml. Linearity was achieved when the standards were analyzed in groups according to the time of incubation. One curve was generated from analysis of samples incubated with chromogenic substrate for 16 minutes, others were generated from analysis of samples incubated with chromogenic substrate for 30 minutes and 60 minutes. Therefore, a standard curve for use in a particular circumstance depended on the sensitivity of the endotoxin measurement that was required.

EXAMPLE 10

Production of Penta-hemoglobin rHb1.1 containing a K158C mutation in the dialpha globin (hereinafter referred to as K158C) was expressed and purified as described above. rHb1.1 was expressed and purified as described in PCT publication number WO 95/14038, filed Nov. 14, 1994, entitled Purification of Hemoglobin." The penta-hemoglobin was then formed by reacting K158C with a core rHb1.1 molecule (that did not contain the K158C mutation) activated as described below.

The core rHb1.1 molecule was activated by reacting with sulfosuccinimidyl 4-(N-maleimidomethyl)cyclohexane-1-carboxylate (sulfo-SMCC) (Pierce Chemicals, Rockford, Ill.). Sulfo-SMCC is a water soluble heterobifunctional crosslinker that reacts with both amine and sulfhydryl functional groups. Reaction with lysine residues on rHb1.1 leads to loss of the sulfosuccinimide group with the formation of a stable amide linkage between the protein and the succinimide moiety. The maleimide residues are highly reactive towards sulfhydryl groups. Therefore, following reaction with sulfo-SMCC, the rHb1.1 has been "activated" at multiple surface lysine residues towards reaction with the surface sulfhydryl residue of K158C. The N-(4-carboxycyclohexylmethylmaleimide) residues are particularly stable to hydrolysis and the "activated" rHb1.1 can thus be manipulated extensively prior to addition of K158C.

The desired extent of modification of rHb1.1 was determined empirically by reaction with K158C following activation. The initial reaction with sulfo-SMCC was modulated by altering the concentration of sulfo-SMCC and reaction time, until a covalent Hb polymer of the desired size range was achieved upon subsequent reaction with K158C. Once determined, these conditions were used throughout. In determining these conditions, the stability of the polymer was monitored.

To activate the rHb1.1 that formed the core of the penta-hemoglobin molecule, a solution of sulfo-SMCC, 10 mg/mL in 100 mM sodium borate buffer pH 8.5, was added to a solution of rHb1.1 (30 mg/mL) at a molar ratio of 35:1 under oxy conditions at 22° C. This was allowed to react for 35 minutes with gentle mixing. The succinimide reactive portion of the crosslinker was then quenched by addition of glycine at a molar ratio of 25:1 (25 M glycine to 1 M crosslnker).

The reaction mixture was then chromatographed on Sephadex G25 equilibrated in 50 mM Tris-HCl buffer, pH 8.0 to remove quenched crosslinker and borate ions and to buffer exchange the activated rHb1.1. Following buffer exchange, the activated rHb1.1 was concentrated to 15 mg/mL and converted into the deoxy form by deoxygenating on a rotary evaporator (ROTOVAP RE111, Brinkmann, Inc., Cuntiague Road, Westbury, N.Y.) flushed with humidified nitrogen.

Following activation of the rHb1.1 molecule, penta-hemoglobin was synthesized as follows. Activated hemoglobin was concentrated to 15 mg/mL and deoxygenated as above. Deoxy activated rHb1.1 was added to previously deoxygenated K158C (60 mg/ml) at a molar ratio of 1 to 5.5 in drop wise fashion. Crosslinking was allowed to proceed spontaneously at room temperature (22° C.) for 3 hours with gentle mixing. The mixture was then cooled to 4° C. and cysteine was added to a final concentration of 8.5 mM and allowed to react for 15 minutes to quench the maleimide portion of the crosslinker. The resultant product contained a mixture of monohemoglobin, dihemoglobin, trihemoglobin, tetrahemoglobin, pentahemoglobin, hexahemoglobin and higher order multimers. Approximately 20% of the mixture was mono- and di-hemoglobin. Approximately 65% of the mixture was most likely tetra-, penta- and hexa-hemoglobin.

The desired molecular weight fraction was resolved from the mixture by size exclusion chromatography on Sephacryl S-200 HR and S-300 HR. Two columns (Pharmacia BPP113, 60 cm length, one of each resin type) were used in series to achieve the desired fractionation. Both columns were equilibrated with phosphate buffered saline, pH 7.5. Alternatively, the molecular weight fractions were separated using ion exchange chromatography as described below.

The pentaHb fraction exhibited the following equilibrium oxygen binding properties: $P_{50}=32$ Torr and $N_{max}=2.1$ on average for multiple determinations.

EXAMPLE 11

Formation of Penta-hemoglobin Using Sulfo-GMBS Crosslinker

Sulfo-GMBS (N-γ-maleimidobutyrloxy)succinimide ester) was dissolved at 10 mg/mi in 100 mM sodium borate, pH 8.5. All other steps were performed identically to the steps disclosed in example 10. The final penta hemoglobin with GMBS crosslinking was produced in approximately the same yield as in example 10.

The pentaHb fraction produced using the GMBS linker exhibited the following equilibrium oxygen binding properties: $P_{50}=30$ Torr and $N_{max}=2.1$ for multiple determinations.

EXAMPLE 12

Formation of Penta-hemoglobin-K158C Core

An entire multimeric Hb-like protein can be prepared using only K158C tetramers. The procedure described in Example 10 can be followed identically. Excess crosslinker is removed by, for example, gel filtration or tangential flow ultrafiltration in the continued presence of borate buffer. Borate buffer should be maintained while sulfhydryl reactive crosslinker is being removed. Following adequate removal of the (amine) quenched crosslinker, the borate buffer is exchanged completely for another suitable buffer, such as Tris-HCl buffer (using, for example, gel filtration or tangential flow ultrafiltration). This readies the material for the final crosslinking step as described in Example 10 in which pentaHb is produced.

EXAMPLE 13

Purification of Glutaraldehyde Crosslinked Hemoglobin by Anion Exchange Chromatography Recombinant hemoglobin (rHb1.1) was expressed, prepared and purified as described in PCT publication number WO 95/14038, filed Nov. 14, 1994, entitled "Purification of Hemoglobin" herein incorporated by reference in its entirety. This hemoglobin (24 g) was concentrated to ~150 mg/ml and deoxygenated in a 1L round bottom flask by purging for 5 hours with humidified nitrogen on a Brinkmann ROTOVAP RE111 (Brinkmann, Inc., Cuntiague Road, Westbury, N.Y.). and crosslinked at 25° C. with a 6:1 molar ratio of glutaraldehyde:rHb1.1 (glutaraldehyde was a 10% aqueous solution, diluted from 25% aqueous solution, Sigma Chemical Company, St. Louis, Mo.). The reaction was terminated after 4 minutes with a 3:1 molar ratio of sodium borohydride: glutaraldehyde then buffer exchanged with ultrafiltration into a 20 mM Tris, pH 8.9 (8° C.) buffer. The crosslinked hemoglobin (21 g) was then loaded onto a 450 ml SEPHAROSE-Q ion-exchange resin. After the column was loaded it was washed 8 CV's of 20 mM Tris, pH 7.6 (8° C.) followed by elution with 20 mM Tris, pH 7.4 (8° C.).

TABLE 3

Protein distribution displayed as % of total in eluted fraction

| | 65 kDa | 128 kDa | 190 kDa | >230 kDa |
|---|---|---|---|---|
| Load | 27.7 | 17.7 | 13.3 | 40.5 (230–5000 kDa) |
| Breakthrough | | | | 99.3 (200–5000 kDa) |
| pH 7.6 Wash | 60.9 | 25.6 | 7.1 | 2.5 (250–535 kDa) |
| pH 7.4 wash | 1.0 | 6.6 | 13.1 | 79.2 (250–2000 kDa) peak = 410 kDa |

EXAMPLE 14

Selective Purification of Glutaraldehyde Crosslinked Hemoglobin Molecular Weight Fractions Using pH Elution Glutaraldehyde crosslinked hemoglobin (~1 g) prepared as described in Example 13 was loaded onto a 50 ml bed volume SEPHAROSE-Q ion-exchange resin. The column was washed with loading buffer as described in the previous example followed by elution of the bound protein with a stepwise pH gradient beginning with a 20 mM Tris buffer, pH 7.8 (8° C.). The pH steps were decreased in 0.1 pH unit increments with only selected fractions shown here for illustration. The use of very small pH increments improved resolution of the different molecular weight fractions.

TABLE 4

Protein distribution displayed as % of total in eluted fraction

| | 65 kDa | 128 kDa | 190 kDa | >230 kDa |
|---|---|---|---|---|
| Load | 30.7 | 19.0 | 13.5 | 36.7 (260–4200 kDa) |
| Load Break (pH 8.9) | | | | 98.0 (260–4200 kDa) peak = 1400 kDa |
| pH 7.8 wash | 92.6 | 5.7 | | |
| pH 7.7 wash | 38.8 | 54.6 | 5.1 | |
| pH 7.5 wash | 7.4 | 20.3 | 29.4 | 41.7 (250–2000 kDa) peak = 285 kDa |
| pH 7.3 wash | 3.5 | 8.2 | 11.2 | 76.6 (250–4200 kDa) peak = 453 kDa |

EXAMPLE 15

Effect of Protein Concentration on Separation Efficiency

Hemoglobin was crosslinked as described in Example 13 and loaded onto a 50 ml bed volume SEPHAROSE-Q ion-exchange resin. The column loads were sequentially increased (Table Five). Loading procedures and elution of the protein was the same as in Example 13. As noted in Table Five below, increasing the hemoglobin load improved the efficiency of separation, particularly in the region of 230–800 kDa molecular weights.

TABLE 5

Protein distribution displayed as % of total protein in eluted fraction

| | 65 kDa | 128 kDa | 190 kDa | 230–800 kDa | >800 kDa |
|---|---|---|---|---|---|
| Load | 31.6 | 19.0 | 13.8 | 24.8 | 10.7 |
| 10 g/L resin | 2.7 | 6.6 | 9.3 | 50.1 | 31.2 |
| 25 g/L resin | 2.6 | 7.3 | 9.9 | 54.2 | 25.9 |
| 50 g/L resin | 1.9 | 7.8 | 11.8 | 57.7 | 20.6 |
| 80 g/L resin | 1.2 | 6.1 | 11.4 | 57.2 | 23.9 |

EXAMPLE 16

Effect of Column Size on Separation

Hemoglobin was crosslinked as described in Example 13 and loaded onto either a 50 ml or 2100 ml bed volume SEPHAROSE-Q ion-exchange resin. The column loads were 30 g/L resin and 14.7 g/L resin for the 50 ml and 2100 ml columns respectively. Protein distributions in each column load were similar to those described previously. Loading and elution of the protein was the same as in Example 14. As noted in Table Six below, there was only a minimal effect of column size on efficiency of separation. Therefore, this methodology can be applicable to any scale of separation.

TABLE 6

Protein distribution displayed as % of total protein in eluted fraction

|  | 65 kDa | 128 kDa | 190 kDa | >230 kDa |
|---|---|---|---|---|
| 50 ml Q-SEPHAROSE column | 2.6 | 9.7 | 15.1 | 72.3 (250–4200 kDa) peak = 328 kDa |
| 2.1 L Q-SEPHAROSE column | 3.9 | 9.1 | 13.0 | 73.6 (250–4200 kDa) peak 426 kDa |

EXAMPLE 17

Selective Purification of Pentameric Hemoglobin Molecular Weight Fractions By Ion Exchange Super Q 650 C (TosoHaas) was equilibrated with 5 CV's of 20 mM Tris pH=8.9. The column was sized at binding of 15 grams protein per liter of resin. The pH and the conductivity of the protein sample were adjusted to match the equilibration buffer and loaded onto the column at approximately 4.5 grams for an approximately 300 ml column. The column was then washed with 2 column volumes of 20 mM Tris pH=8.9, followed by 7–8 CV wash 25 mM Bis-Tris/Tris pH=7.5, which allowed for removal of monomeric hemoglobin. The column was eluted using 25 mM Bis-Tris/Tris, 100 mM NaCl pH=7.5. After this purification, only approximately 3% monomeric hemoglobin remained in the purified pentahemoglobin solution, indicating a 5–6 fold purification across the anion exchange step.

The foregoing description of the invention is exemplary for purposes of illustration and explanation. It will be apparent to those skilled in the art that changes and modifications are possible without departing from the spirit and scope of the invention. It is intended that the following claims be interpreted to embrace all such changes and modifications.

What is claimed is:

1. A globin-like polypeptide comprising two dialpha domains.

2. The globin-like polypeptide of claim 1, wherein said polypeptide contains a non-naturally occurring cysteine residue.

3. A hemoglobin-like molecule comprising at least two connected globin-like polypeptides of claim 1, wherein said connection consists of direct connection through a disulfide bond or indirect connection through a chemical crosslinker selected from the group consisting of homobifunctional linkers, heterobifunctional linkers, homopolyfunctional linkers and heteropolyfunctional linkers.

4. The globin-like polypeptide of claim 2, wherein said non-naturally occurring cysteine residue is asymmetric.

5. A multimeric hemoglobin-like protein comprising a core hemoglobin-like moiety to which each of at least two other hemoglobin-like moieties are directly attached to the core hemoglobin-like moiety.

6. The multimeric hemoglobin-like protein of claim 5, wherein the other hemoglobin-like moieties are attached to the core hemoglobin-like moiety by a chemical crosslinker.

7. The multimeric hemoglobin-like protein of claim 5, wherein the other hemoglobin-like moieties are attached to the core hemoglobin-like moiety by a N-γ-maleimidobutyrloxysuccinimide ester.

8. The multimeric hemoglobin-like protein of claim 7, wherein the core hemoglobin-like moiety is rHb1.1 and the other hemoglobin-like moieties are K158C.

9. A method for separation of molecular weight fractions of polymerized hemoglobin-like molecules to obtain substantially monodisperse hemoglobin solutions comprising:

(a) contacting a polydisperse mixture of polymerized hemoglobin-like molecules with an ion exchange matrix;

(b) washing the ion exchange matrix with a first buffer;

(c) eluting the ion exchange matrix with a second buffer which can be the same or different from said first buffer to obtain a substantially monodisperse hemoglobin-like solution.

10. The method of claim 9, wherein the ion exchange matrix is an anion exchange matrix.

* * * * *